US006730495B2

(12) United States Patent
Selitrennikoff et al.

(10) Patent No.: US 6,730,495 B2
(45) Date of Patent: May 4, 2004

(54) METHODS FOR THE IDENTIFICATION OF ANTIMICROBIAL COMPOUNDS

(75) Inventors: Claude P. Selitrennikoff, Evergreen, CO (US); Mitsunori Nakata, Denver, CO (US)

(73) Assignee: Mycologics, Inc., Denver, CO (US)

( * ) Notice: Subject to any disclaimer, the term of this patent is extended or adjusted under 35 U.S.C. 154(b) by 0 days.

(21) Appl. No.: 09/866,209

(22) Filed: May 25, 2001

(65) Prior Publication Data

US 2002/0177182 A1 Nov. 28, 2002

(51) Int. Cl.[7] ................................................ C12Q 1/18
(52) U.S. Cl. ........................... 435/32; 435/14; 435/69.2
(58) Field of Search ............................. 435/32, 14, 29, 435/69.1, 69.2

(56) References Cited

U.S. PATENT DOCUMENTS 5,998,420 A  * 12/1999 Grandoni .................... 514/256
6,355,616 B1 *  3/2002 Little, II et al. .............. 514/14
6,372,476 B1 *  4/2002 Belguith et al.

OTHER PUBLICATIONS

Milewski S. Anticapsin Drugs Exptl Clin Res 12(6–7)577–583, 1986.*
Silitrennikoff C. Emerging Therapeutic Cell Wall Targets in Fungal Infections. Emerging Therapeutic Targets 3:53–72, 1999.*
Phobe C. Extremophilic Organisms in an Unexplored Source of Antifungal Compounds. J of Antibiotics 54(1)56–65, Jan. 2001.*
Anaissie, "Opportunistic mycoses in the immunocompromised host: experience at a cancer center and review," *Clin. Infect. Dis.*, 14(Suppl 1):S43–S53 (1992).
Ausubel et al. (eds.), *Current Protocols in Molecular Biology*, vols. 1–4, (New York: John Wiley & Sons, Inc.) [1994] title and copyright pages supplied, cover pages only.
Badet et al., "Glucosamine synthetase from *Escherichia coli:* Purification, properties, and glutamine–utilizing site location," *Biochemistry* 26:1940–1948 [1987].
Beck–Sague et al.,"Secular trends in the epidemiology of nosocomial fungal infections in the United States, 1980–1990," *J. Infect. Dis.*, 167:1247–1251 [1993].
Borgia, "Roles of the orlA, tsE, and bimG genes of *Aspeergillis nidulans* in chitin synthesis," *J. Bacteriol.*, 174:384–389 [1992].
Boschman et al., "Thirteen–year evolution of azole resistance in yeast isolates and prevalence of resistant strains carried by cancer patients at a large medical center," *Antimicrob. Agents Chemother.*, 42:734–738 [1998].
Boshart et al., "A very strong enhancer is located upstream of an immediate early gene of human cytomegalovirus," *Cell* 41:521–530 [1985].

Bow, "Invasive fungal infections in patients receiving intensive cytotoxic therapy for cancer," *Br. J. Haematol.*, 101(Suppl 1):1–4 [1998].
Brooks et al, (ed.), *Jawetz, Melnick & Adelberg's Medical Microbiology*, 19th edition, (Norwalk, CT: Appleton & Lange) p. 150 [1991].
Bulawa, "Genetics and molecular biology of chitin synthesis in fungi,"*Annu. Rev. Microbiol.*, 47:505–534 [1993].
Cohen et al., "Nonchromosomal antibiotic resistance in bacteria: genetic transformation of *Escherichia coli* by R–factor DNA," *Proc. Natl. Acad. Sci. USA* 69:2110–2114 [1972].
Cole, "Basic biology of fungi," In Baron (ed.) *Medical Microbiology*, 4th edition, (Galveston, TX: University of Texas Medical Branch) pp. 903–911 [1996].
Daniels et al., "Glutamine:fructose–6–phosphate amidotransferase activity in cultured human skeletal muscle cells," *J. Clinical Invest.*, 97(5):1235–1241 [1996].
Decker et al., "Structure–activity relationships of the nikkomycins," *J. Gen. Microbiol.*, 137:1805–1813 [1991].
Denning et al., "Pulmonary aspergillosis is the acquired immunodeficiency syndrome," *New Eng. J. Med.*, 324:654–662 [1992].
Dijkema et al., "Cloning and expression of the chromosomal immune interferon gene of the rat," *EMBO J.*, 4:761–767 [1985].
Dixon and Walsh, "Antifungal Agents," In Baron (ed.) *Medical Microbiology*, 4th edition, (Galveston, TX: University of Texas Medical Branch) pp. 926–932 [1996].
Endo et al., "Feedback inhibition of L–glutamine D–fructose 6–phosphate amidotransferase by uridine diphosphate N–acetylglucosamine in *Neurospora crassa,*" *J. Bacteriol.*, 103:588–594 [1970].
Espinel–Ingroff et al., "Antifungal agents and susceptibility tests," in Murray et al., (eds.), *Manual of Clinical Microbiology*, 7th edition, (Washington, DC: ASM Press) pp. 1640–1652 [1999].
Etchebehere and Da Costa Maia, "Phosphorylation–dependent regulation of aminotransferase during development of *Blasiocladiella emersonii,*" *Arch. Biochem. Biophys.*, 272:301–310 [1989].
Etchebehere et al., "Development regulation of hexosamine biosynthesis by protein phosphates 2A and 2C in *Blastocladiella emersonii,*" *J. Bacteriol.*, 175:5022–5027 [1993].

(List continued on next page.)

Primary Examiner—Ralph Gitomer
(74) Attorney, Agent, or Firm—Medlen & Carroll LLP

(57) ABSTRACT

The present invention relates to methods to assay 2-amino-2-deoxy-D-glucose-6-phosphate ketol-isomerase activity. The present invention also relates to methods for drug screening to identify compounds having antimicrobial activity, wherein the compounds have the ability to inhibit the enzymatic activity of a microbial ketol-isomerase. In other embodiments, methods are provided for the identification of compounds that selectively inhibit microbial ketol-isomerase activity compared to the ketol-isomerase activity of the subject being treated for an infection.

24 Claims, 5 Drawing Sheets

OTHER PUBLICATIONS

Russell and Srb, "A study of L–glutamine–D–fructose 6–phosphate amidotransferase in certain developmental mutants of *Neurospora crassa,*" *Molec. Gen. Genet.,* 129:77–86 [1974].

Sambrook et al. (eds.), *Molecular Cloning: A Laboratory Manual,* 2nd edition, vols. 1–3, (NY: Cold Spring Harbor Laboratory Press) [1989] title and copyright pages supplied.

Selitrennikoff and Ostroff, "Emerging therapeutic cell wall targets in fungal infections," *Emerging Therapeutic Targets* 3:53–72 [1999].

Selitrennikoff and Sonneborn, "Post–translational control of de Novo cell wall formation during *Blastocladiella emersonii* zoospore germination," *Develop. Biol.,* 54:37–51 [1976].

Selitrennikoff and Sonneborn, "The last two pathway–specific enzyme activities of hexosamine biosynthesis are present in *Blastocladiella emersonii* zoospores prior to germination," *Biochim. Biophys. Acta.,* 451:408–416 [1976].

Selitrennikoff et al., "Regulation of the hexosamine biosynthetic pathway in the water mold *Blastocladiella emersonii:* sensitivity to endproduct inhibition is dependent upon the life cycle phase," *Proc. Natl. Acad. Sci. USA* 77:5998–6002 [1980].

Sessegolo et al., "Distribution of serotypes and antimicrobial resistance of *Streptococcus pneumoniae* strains isolated in Brazil from 1988 to 1992," *J. Clin. Microbiol.,* 32:906–911 [1994].

Sigler and Kennedy, "Aspergillus, Fusarium, and other opportunistic moniliaceous fungi," In Murray et al. (eds.), *Manual of Clinical Microbiology,* 7th edition, (Washington DC: ASM Press) pp. 1213–1241 [1999].

Smith et al., "Isolation and characterization of the GFA1 gene encoding the glutamine:fructose–6–phosphate amidotransferase of *Candida albicans,*" *J. Bacteriol.,* 178:2320–2327 [1996].

Tenover and McGowan, "Reasons for the emergence of antibiotic resistance," *Am. J. Med. Sci.,* 311:9–16 [1996].

Tokumura and Horie, "Kinetics of nikkomycin Z degradation in aqueous solution and in plasma," *Biol. Pharm. Bull.,* 20:577–580 [1997].

Tumidge and Jorgensen, "Antimicrobial susceptibility testings: general considerations," In Murray et al. (eds.), *Manual of Clinical Microbiology,* 7th edition, (Washington, DC: ASM Press) pp. 1469–1473 [1999].

Uetsuki et al., "Isolation and characterization of the human chromosomal gene for polypeptide chain elongation factor–1α," *J. Biol. Chem.,* 264:5791–5798 [1989].

Van Noorden and Butcher, "The involvement of superoxide anions in the nitro blue tetrazolium chloride reduction mediated by NADH and phenazine methosulfate," *Anal. Biochem.,* 176:170–174 [1989].

Voss et al., "The role of enhancers in the regulation of cell–type–specific transcriptional control," *Trends Biochem. Sci.,* 11:287–289 [1986].

Walsh and Dixon, "Spectrum of mycoses," In Baron (ed.), *Medical Microbiology,* 4th edition, (Galveston, TX: University of Texas Medical Branch) pp. 919–925 [1996].

Warnock, "Fungal infections in neutropenia: current problems and chemotherapeutic control," *J. Antimicrob. Chemother.,* 41:95–105 [1998].

Warren and Hazen, "Candida, Cryptococcus, and other yeasts of medical importance," In Murray et al. (eds.), *Manual of Clinical Microbiology,* 7th edition, (Washington, DC: ASM Press) pp. 1184–1199 [1999].

Watzele and Tanner, "Cloning of the glutamine:fructose–6–phosphate amidotransferase gene from yeast," *J. Biol. Chem.,* 264:8753–8758 [1989].

White, "Antifungal drug resistance in *Candida albicans,*" *ASM News* 63:427–433 [1997].

White et al., "Clinical, cellular, and molecular factors that contribute to antifungal drug resistance," *Clin. Microbiol. Rev.,* 11:382–402 [1998].

Winterburn and Phelps, "Purification and some kinetic properties of rat liver glucosamine synthetase," *Biochem. J.,* 121:701–709 [1971].

Zalkin, "Glucosamine–6–phosphate synthase," *Methods Enzymol.,* 113:278–281 [1985].

Ferraro and Jorgensen, "Susceptibility testing instrumentation and computerized expert systems for data analysis and interpretation," In Murray et al., (eds.), *Manual of Clinical Microbiology,* 7th edition, (Washington, DC: ASM Press) pp. 1593–1600 [1999].

Goodwin et al., "A nationwide survey of clinical laboratory methodologies for fungal infections," *J. Med. Vet. Mycol.,* 30:153–160 [1992].

Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1982].

Graham and van der Eb, "A new technique for the assay of infectivity of human adenovirus 5 DNA," *Virol.,* 52:456–467 [1973].

Graybill, "The future of antifungal therapy," *Clin. Infect. Dis.,* 22(Suppl 2):S166–S178 [1996].

Hanahan, "Studies on transformation of *Escherichia coli* with plasmids," *J. Mol. Biol.,* 166:557–580 [1983].

Hanson et al., "Synergy between cilofungin and amphotericin B in a murine model of candidiasis," *Antimicrob. Agents Chemother.,* 35:1334–1337 [1991].

Inderlied and Salfinger, "Antimycobacterial agents and susceptibility tests," In Murray et al., (eds.), *Manual of Clinical Microbiology,* 7th edition, (Washington, DC: ASM Press) pp. 1601–1623 [1999].

Jorgensen et al., "Antibacterial susceptibility tests: dilution and disk diffusion methods," In Murray et al. (eds.), *Manual of Clinical Microbiology,* 7th edition, (Washington, DC: ASM Press) pp. 1526–1543 [1999].

Katz and Rosenberger, "A mutation in *Aspergillus nidulans* producing hyphal walls which lack chitin," *Biochim. Biophys. Acta.,* 208:452–460 [1970].

Kim et al., "Use of the human elongation factor 1αpromoter as a versatile and efficient expression system," *Gene* 91:217–223 [1990].

Kornfeld, "Studies on L–glutamine, D–fructose 6–phosphate amidotransferase," *J. Biol. Chem.,* 242:3135–3141 [1967].

Leloir and Cardini, "The biosynthesis of glucosamine," *Biochim. Biophys. Acta.,* 12:15–22 [1953].

Lortholary et al., "Invasive aspergillosis in patients with acquired immunodeficiency syndrome: report of 33 cases," *Amer. J. Med.,* 95:177–187 [1993].

Maniatis et al., "Regulation of inducible and tissue–specific gene expression," *Science* 236:1237–1244 [1987].

McGinnis and Tyring, "Introduction to Mycology," In Baron (ed.), *Medical Microbiology,* 4th edition, (Galveston TX: University of Texas Medical Branch) pp. 893–902 [1996].

McKnight et al., "Molecular cloning, cDNA sequence, and bacterial expression of human glutamine:fructose–6–phosphate amidotransferase," *J. Biol. Chem.,* 267:25208–25212 [1992].

Mellado et al., "A multigene family related to chitin synthase genes of yeast in the opportunistic pathogen *Aspergillus fumigatus,*" *Mol. Gen. Genet.,* 246:353–359 [1995].

Meunier, et al., "Candidemia in immunocompromised patients," *Clin. Infect. Dis.,* 14(Suppl 1):S120–S125 [1992].

Milewski et al., "Antifungal peptides with novel specific inhibition of glucosamine 6–phosphate synthase," *Drugs Exp. Clin. Res.,* 14:461–465 [1988].

Milewski et al., "Mechanism of action of anticandidal dipeptides containing inhibitors of glucosamine–6–phosphate synthase," *Antimicrob. Agents Chemo.,* 35:36–43 [1991].

Milewski et al., "Oligomeric structure and regulation of *Candida albicans* glucosamine–6–phosphate synthase," *J. Biol. Chem.,* 274(7):4000–4008 [1999].

Miller et al., "Pulmonary aspergillosis in patients with AIDS," *Chest* 105:37–44 [1994].

Mitchell, "Opportunistic mycoses," in Joklik et al. [eds], *Zinsser Microbiology,* (Norwalk, CT; Appleton, Century–Crofts) pp. 1183–1197 [1984].

Mizushima and Nagata, "pEF–BOS, a powerful mammalian expression vector," *Nuc. Acids. Res.,* 18:5322 [1990].

National Committee for Clinical Laboratory Standards (NCCLS), "Reference Method for Broth Dilution Susceptibility Testing of Yeasts: Tentative Standard," Publicaion M27–T [1995].

Polis and Kovacs, "Fungal Infections in Patients with the Acquired Immunodeficiency Syndrome," in DeVita et al. (eds), *AIDS: Biology, Diagnosis, Treatment, and Prevention,* 4th ed., (Philadelphia, PA: Lippincott–Raven Publishers) pp. 231–244 [1997].

* cited by examiner

METHODS FOR THE IDENTIFICATION OF ANTIMICROBIAL COMPOUNDS

FIELD OF THE INVENTION

The present invention relates to methods for the assay of 2-amino-2-deoxy-D-glucose-6-phosphate ketol-isomerase activity. The present invention also relates to methods for drug screening to identify compounds having antimicrobial activity, wherein the compounds have the ability to inhibit the enzymatic activity of microbial ketol-isomerase.

BACKGROUND

Microbial infections (e.g., infections by fungal or bacterial species) account for significant morbidity and mortality throughout the world. Although significant resources have been dedicated to identifying compounds having antimicrobial properties, microbial infections continue to present a significant human health risk in both developed and undeveloped countries.

Bacterial Infections and Drug Resistance

The development of antibacterial agents, starting with the identification of penicillin in the 1920s, has played a vital role in the treatment of human infectious diseases. However, the recent emergence of pathogenic microorganisms that are resistant to known antimicrobial compounds is cause for great concern. This situation has resulted from prolonged, worldwide use of antimicrobial compounds, with the unfortunate effect of selection of resistant microorganisms. For example, penicillin resistance has become increasingly widespread in the bacterial species that were previously susceptible to the drug. Some microorganisms produce β-lactamase, an enzyme which destroys the antimicrobial agent itself, while some microorganisms have undergone genetic changes resulting in alterations in the cell receptor protein to which the penicillin binds (i.e., penicillin-binding proteins; PBPs; *Jawetz, Melnick & Adelberg's Medical Microbiology*, 19th ed, Appleton & Lange, Norwalk, Conn. [1991], p. 150), such that the drugs will no longer effectively bind to the receptors. Still other microorganisms have evolved mechanisms that prevent lysis of the organism after the drug has bound to the cell. In this latter scenario, the drug inhibits the growth of the organism, but the organism is not killed, and relapse of disease occurs following discontinuation of treatment.

One well-documented example highlighting the problem of drug resistance is the development of penicillin resistance in the pathogenic bacterium *Streptococcus pneumoniae*. Initially, the introduction of penicillin to treat *S. pneumoniae* resulted in a significant decrease in the mortality due to this organism. However, *S. pneumoniae* infection remains of great concern, as it is one of the organisms most frequently associated with invasive infections; it is the most common cause of bacterial pneumonia and otitis media, as well as the second most common cause of bacterial meningitis, and the third most common isolate from blood cultures (Sessegolo et al., *J. Clin. Microbiol.*, 32:906–911 [1994]).

The first report of pneumococci with decreased susceptibilities to penicillins occurred in 1967 in Australia. Since this initial report, additional strains with decreased susceptibilities have been reported worldwide. Additionally, bacterial resistance to alternative antibacterial compounds, such as chloramphenicol, erythromycin, tetracycline, clindamycin, rifampin, and sulfamethoxazole-trimethoprim has also been reported, often in conjunction with penicillin resistance. Multiple-antimicrobial resistance in pneumococci was first reported in 1977 in South Africa. Since this initial report, multi-drug resistant strains have been reported in several other countries, including Spain, Italy, France, Belgium, Hungary, Pakistan, Czechoslovakia, Canada, the United Kingdom, and the United States (Sessegolo et al., *J. Clin. Microbiol.*, 32:906–911 [1994]).

A second example illustrating the evolution of a multiple drug-resistant organism is *Nisseria gonorrhoeae*, the causative agent of gonorrhea. Prior to the 1930s, treatment for this disease was largely ineffective. In the late 1930s, sulfonamide antibacterials were found to be effective in treating gonorrhea. A few years thereafter, sulfonamide-resistant strains of *N. gonorrhoeae* were identified. Fortunately, by this time, penicillin was available and found to be effective against these infections. However, by the 1970's, many isolates of *N. gonorrhoeae* were found to be penicillin-resistant, requiring the use of additional, alternative drugs such as spectinomycin. It can be expected that this trend will continue, with the development of strains that are resistant to sulfonamides, penicillin, spectinomycin, and other antimicrobials.

Multiple drug resistance has been reported in a large number of clinically significant bacterial species, including *Escherichia coli, Klebsiella pneumoniae, Pseudomonas aeruginosa, Haemophilus influenzae, Neisseriae gonorrhoeae, Staphylococcus aureus, Staphylococcus hemolyticus*, and *Streptococcus pneumoniae*. Many of these organisms are isolated from hospital environments. The development of multi-drug-resistance of nosocomial (hospital-acquired) and community-acquired pathogens to antimicrobial agents is a significant public health concern with both clinical and economic consequences.

Alarmingly, in the past few years, a handful of organisms resistant to all known antimicrobial agents has emerged (Tenover et al., *Am. J. Med. Sci.*, 311:9–16 [1996]). Though such organisms are rare, the existence of conditions favoring the development and spread of these organisms forecasts the continued emergence of multi-drug resistance. This problem is further exacerbated by the scarcity of new classes of antimicrobial agents, since many pharmaceutical manufacturers have abandoned the discovery of antimicrobial drugs in favor of more profitable products.

Fungal Infections and Drug Resistance

Fungal organisms have become increasingly significant pathogens in immunocompromised patients, especially those who because of cancer, organ transplantation, chemotherapy, pregnancy, age, diabetes, complications following extensive surgery, and various immune system dysfunctions, are at risk of experiencing life-threatening diseases caused by microorganisms which do not ordinarily pose a threat to normal, immunocompetent people. Other risk factors for deeply invasive fungal infections include protracted treatment using broad spectrum antimicrobials, corticosteroids, and vascular catheters.

Indeed, immunocompromised patients provide a significant challenge to modern health care delivery. For example, fungal infections have become one of the leading factors contributing to morbidity and mortality in cancer patients, and fungi account for 4–12% of nosocomial pathogens in leukemia patients (Anaissie, *Clin. Infect. Dis.*, 14[Suppl.1]: S43 [1992]). The incidence of nosocomial bloodstream infections with fungi such as Candida spp. ("candidemia") has increased in recent years and has been reported to account for 5.6% of all primary bloodstream infections. There are an estimated 200,000 patients/year who acquire nosocomial fungal infections, with bloodstream infections having a mean mortality rate of 55% (See e.g., Beck-Sague et al., *J. Infect. Dis.,* 167:1247 [1993]; and the Centers for Disease Control website at www.cdc.gov/ncidod/publications/brochures/hip.html). Fungal infections in non-humans, such as livestock and agricultural products, is also of significant health and economic concern. The most common fungal pathogens in humans are the opportunistic yeast, *Candida albicans* and the filamentous mold, *Aspergillus fumigatus* (See, Bow, *Br. J. Haematol.,* 101:1 [1998]; and Warnock, *J. Antimicrob. Chemother.,* 41:95 [1998]).

*C. albicans* is the most common fungal pathogen in humans, with other Candida species becoming increasingly important in fungal disease in humans and other animals (See, Walsh and Dixon, "Spectrum of Mycoses," in Baron [ed.], *Medical Microbiology,* 4th ed, University of Texas Medical Branch, Galveston, Tex. [1996], pp. 919–925). Approximately 200 Candida species are known, with approximately seven of those species isolated with significant frequency from human specimens (See, Warren and Hazen, Ch. 95, pp. 1184–1199, "Candida, Cryptococcus, and Other Yeasts of Medical Importance," in Murray et al., [eds], *Manual of Clinical Microbiology,* 7th ed., ASM Press, Washington, D.C. [1999]; and Mitchell, in *Zinsser Microbiology,* Joklik et al., [eds], Appleton, Century-Crofts, Norwalk, Conn., pp. 1183–1190 [1984]).

The clinical manifestations of Candida infections and disease are many and varied, as Candida species are known to invade most organ systems of the body. Superficial candidiasis may involve the epidermal and mucosal surfaces (e.g., the oral cavity, pharynx, esophagus, intestines, urinary bladder, and vagina). In deep candidiasis, the gastrointestinal tract and intravascular catheters are the two major portals of entry, with the kidneys, liver, spleen, brain, eyes, heart, and other tissues being the major sites involved.

The major difficulties in treating Candida infections are encountered in cases of systemic disease. Chronic mucocutaneous, pulmonary candidiasis, endocarditis, and fungemia must be diagnosed early in order to avoid fatality. The incidence of candidiasis in certain patient populations is striking. Up to 30% of leukemia patients acquire systemic candidiasis (Anaissie, *Clin. Infect. Dis.,* 14[Suppl.1]:S43 [1992]). This is of great significance, as some reports indicate that the fatality rate for disseminated candidiasis in cancer patients is as high as 80% (Meunier, et al., *Clin. Infect. Dis.,* 14[Suppl. 1]:S120 [1992]).

Aspergillus species are the second most common isolate, after Candida species, in patients with positive fungal cultures (See, Sigler and Kennedy, Ch. 97, "Aspergillus, Fusarium, and Other Opportunistic Moniliaceous Fungi," in Murray et al., (eds), *Manual of Clinical Microbiology,* 7th ed., ASM Press, Washington, D.C. [1999], pp. 1213–1241; and Goodwin et al, *J. Med. Vet. Mycol.,* 30:153 [1992]). A large number of species of the genus Aspergillus have clinical relevance, although *A. fumigatus, A. niger* and *A. flavus* are most commonly isolated. Of these isolates, *A. fumigatus* is the most common human pathogen. Three main types of disease have been associated with *A. fumigatus,* namely allergic asthma, aspergilloma, and invasive aspergillosis (See e.g., Lortholary et al., *Amer. J. Med.,* 95:177–187 [1993]).

Allergic pulmonary asthma due to *A. fumigatus* exposure affects an estimated 50,000 individuals in the U.S. Aspergillomas are formed when fungal spores germinate in situ in tissue such as the lungs and form fungus balls. There is typically no invasion of underlying tissues, and in most cases treatment involves the simple surgical removal of the aspergilloma. However, invasive aspergillosis involves the invasion of host tissues, and is most commonly observed in patients with predisposing conditions (e.g., immunosuppressive drugs, neutropenia, chemotherapy, AIDS). Transplant (e.g., bone marrow or organ) and chemotherapy patients are at the greatest risk for this form of aspergillosis (See e.g., Denning et al., *New Eng. J. Med.,* 324:654–662 [1992]; and Miller et al., *Chest* 105:37–44 [1994]). The prognosis for patients with invasive aspergillosis is particularly grave, with mortality rates greater than 50% (See e.g, Polis et al., "Fungal Infections in Patients with the Acquired Immunodeficiency Syndrome," in DeVita et al. (eds), *AIDS: Biology, Diagnosis Treatment and Prevention,* 4th ed., Lippincott-Raven, [1997]), due to the lack of a rapid diagnostic method to confirm *A. fumigatus* infection, and the lack of safe antifungal drugs.

The development of effective antifungal agents has lagged behind that of antibacterial agents. Fungi, like humans, are eukaryotic. Thus, most agents that have antimicrobial activity towards fungi are also toxic to humans (i.e., due to non-selective toxicity). Four general groups of antifungals have been developed; these are the polyenes, the azoles, the allylamines/morpholines, and the antimetabolites. Despite the identification of cell membrane, cell wall, and microtubule targets for antifungal action, antifungal development has been slow.

The polyene antifungals (e.g., amphotericin B and nystatin) target the fungal cell membrane, which is similar to mammalian plasma membranes, with the exception being that fungal plasma membranes contain ergosterol, rather than cholesterol as the principal sterol. The polyene amphotericin B remains the treatment mainstay for life-threatening and other mycoses, including candidiasis, cryptococcosis, aspergillosis, zygomycosis, coccidioidomycosis, histoplasmosis, blastomycosis, and paracoccidioidomycosis. Amphotericin B must be administered intravenously and is associated with numerous, often serious side effects, including phlebitis at the infusion site, fever, chills, hypokalemia, anemia, nephrotoxicity and hypokalemia. Nystatin is another broad-spectrum polyene antifungal. However, its toxicity to humans prevents its widespread use. Currently, it is limited to topical applications, where it is effective against yeasts, including *C. albicans.*

The azole antifungals (e.g., fluconazole, itraconazole, imidazole and ketoconazole) and the allylamine and morpholine antifungals (e.g., naftifine and terbinafine) interfere with ergosterol biosynthesis. Ketoconazole may be used to treat histoplasmosis, blastomycosis, mucosal candidiasis and various cutaneous mycoses (e.g., dermatophyte infections, pityriasis versicolor, and cutaneous candidiasis). However, it is not useful for treatment of aspergillosis or systemic yeast infections. Side effects associated with use of the azoles are not as severe as those associated with amphotericin B, although life-threatening hepatic toxicity may result from long-term azole use. Other side effects include nausea, vomiting, and drug interactions with such compounds as cyclosporin, antihistamines, anticoagulants, antiseizure and oral hypoglycemic medications.

The few antimetabolite antifungals identified have not found widespread use. The most commonly used antifungal is 5-fluorocytosine, a fluorinated analog of cytosine. However, as with other antimetabolites, drug resistant fungal strains have emerged, and 5-fluorocytosine is seldom used alone. Nonetheless, in combination with amphotericin B, it remains the treatment of choice for cryptococcal meningitis, and is effective against some diseases caused by dematiaceous fungi.

Griseofulvin, an antifungal compound produced by *Penicillium griseofulvin,* acts by targeting microtubule-associated proteins. Griseofulvin is active against most dermatophytes, and is commonly used to treat dermatophytic infections. Potassium iodide is another compound that is used as an antifungal to enhance transepidermal elimination of fungal organisms in cases of cutaneous and lymphocutaneous sporotrichosis, although it is not effective against *Sporothrix schenckii* in vitro.

As in bacteria, drug-resistant strains of fungal pathogens have also been reported. This drug resistance can take various forms, such as primary resistance, where the susceptibility profiles for the species are characteristic, inherent, and rarely change in response to drug exposure, or the resistance can be secondary (i.e., acquired). Some of the molecular and cellular mechanisms by which fungal organisms acquire resistance are known (White, *ASM News* 63:427–433 [1997]; and White et al., *Clin. Microbiol. Rev.*, 11:382–402 [1998]).

Significantly, fungal resistance to amphotericin B has been reported for various opportunistic fungi, including *Pseudallescheria boydii*, Fusarium, Trichosporon, and some *C. lusitaniae* and *C. guilliermondii* isolates (See, Dixon and Walsh, "Antifungal Agents," in Baron (ed.), *Medical Microbiology*, 4th ed., University of Texas Medical Branch, Galveston, Tex. [1996], pp. 926–932). In addition, the emergence of azole-resistant fungal strains has raised concerns regarding use of the azole compounds, especially fluconazole, as a front-line treatment regime (Boschman et al., *Antimicrob. Agents Chemother.*, 42:734 [1998]; Graybill, *Clin. Infect. Dis.*, 22(Suppl.2):S166 [1996]; White, *ASM News* 63:427–433 [1997]; and White et al., *Clin. Microbiol. Rev.*, 11:382–402 [1998]).

In view of the development of resistance, as well as the relative lack of variety available in the selection of antifungals, there remains a need for the development of compounds useful for treatment of fungal diseases.

Selective Toxicity

The principle of selective toxicity is fundamental to the development of successful antimicrobial agents. That is to say, an antimicrobial compound, while toxic to the microorganism, ideally is not toxic to the subject receiving the antimicrobial compound. Selective toxicity is often a reflection of differences between the microorganism and host physiologies.

One approach to achieving selective toxicity is to identify a compound that is able to inhibit an essential enzyme in the microorganism, but due to differences in enzyme structure or function, that same antimicrobial compound does not affect the homologous enzyme in the host. Alternatively, an antimicrobial compound can inhibit a biochemical event that is essential to the microorganism, but that biochemical process may not be present or be essential to the host.

For example, penicillin, like all β-lactam antibacterial drugs, is a compound that selectively inhibits bacterial cell wall synthesis. The initial step in the mechanism of action of these β-lactam drugs involves the binding of the drug to cell receptors known as "penicillin-binding proteins" (PBPs) (*Jawetz, Melnick & Adelberg's Medical Microbiology*, 19th ed, Appleton & Lange, Norwalk, Conn. [1991], p. 150). After binding to the PBP, the drug inhibits the synthesis of peptidoglycan, an essential component in the bacterial cell wall. This results in the eventual triggering of an autolytic cascade leading to cell lysis. Furthermore, these β-lactam drugs are remarkably non-toxic to humans and other animals, due to the absence of peptidoglycans in animal cells.

Chitin Biosynthesis

The fungal cell wall is essential for the viability of the organism, and is a rigid, stratified structure consisting of chitinous microfibrils and polysaccharides, among other components. The cell wall provides support and shape to the cell, and prevents osmotic lysis of the cell. Indeed, even a small lesion within the cell wall can lead to the extrusion of cytoplasm due to the positive intracellular pressure (See, Cole, "Basic Biology of Fungi, in Baron (ed.), *Medical Microbiology*, 4th ed., University of Texas Medical Branch, Galveston, Tex. [1996], pp. 903–911). The yeast form of the *C. albicans* cell wall contains approximately 30–60% glucan, 25–50% mannan (mannoprotein), 1–2% chitin, 2–14% lipid, and 5–15% protein (McGinnis and Tyring, "Introduction to Mycology," in Baron (ed.), *Medical Microbiology*, 4th ed., University of Texas Medical Branch, Galveston, Tex. [1996], pp. 893–902). The chitin within the fungal cell wall is a (β 1–4)-linked polymer of N-acetyl glucosamine (GlcNAc) polymerized by chitin synthase at the plasma membrane (See, FIG. 1).

Chitin, although a minor component of yeast and filamentous fungal cell walls, is essential for cell viability and mother-daughter cell separation. Chitin biosynthesis, which requires uridine diphosphate-N-acetyl glucosamine (UDP-GlcNAc), is complex and is catalysed by at least three gene products in *S. cerevisiae*, and perhaps as many as six gene products in certain filamentous molds (Bulawa, *Ann. Rev. Microbiol.*, 47:505–534 [1993]; and Mellado et al., *Mol. Genet.*, 246:353–359 [1995]). The three yeast genes, csI, csII and csIII, each have homologues in *C. albicans* and each performs a different intracellular function.

UDP-GlcNAc is the substrate for chitin synthase. Normal levels of UDP-GlcNAc are required for chitin biosynthesis and subsequent cell wall assembly and growth (Katz and Rosenberger, *Biochim. Biophys. Acta.*, 208:452–460 [1970]). The pathway for the synthesis of UDP-GlcNAc, known as the Leloir pathway (Leloir and Cardini, *Biochim. Biophys.* Acta., 12:15–22 [1953]) is shown in FIG. 1. In this Figure, chitin synthase activity is shown for context, but is not considered part of the Leloir pathway. The first pathway-specific enzyme is 2-amino-2-deoxy-D-glucose-6-phosphate ketol-isomerase (known simply as ketol-isomerase; E.C. 5.3.1.19 or E.C. 2.6.1.16). The ketol-isomerase is an amino transferase that forms glucosamine-6-phosphate (GlcN-6-P) and glutamate from fructose-6-phosphate and glutamine (Selitrennikoff and Sonneborn, *Develop. Biol.*, 54:37–51 [1976]). The second enzyme in the pathway is aminodeoxyglucosephosphate acetyltransferase (E.C. 2.4.1.4), which converts S-acetyl CoA and GlcN-6-P to CoA and N-acetylglucosamine-6-phosphate (GlcNAc-6-P) (Selitrennikoff and Sonneborn, *Develop. Biol.*, 54:37–51 [1976]). The third enzyme is acetylaminodeoxyglucose phosphomutase (also known as GlcNAc-phosphomutase; E.C. 2.7.5.2) which converts GlcNAc-6-P to GlcNAc-1-phosphate, employing Glc-1,6-phosphate as a co-factor. The most downstream enzyme is UTP:acetylaminodeoxyglucose-1-phosphate uridylyl transferase (E.C. 2.7.7.23), which converts UTP and GlcNAc-1-phosphate to UDP-GlcNAc and pyrophosphate ($PP_i$) (Selitrennikoff and Sonneborn, *Biochim. Biophys.* Acta., 451:408–416 [1976]; and Etchebehere et al., *J. Bacteriol.*, 175:5022–5027 [1993]).

Chitin synthase has been a target for the identification of antifungal compounds for over 30 years, yet only two classes of compounds that target this enzyme have been identified. These are the competitive substrate inhibitors, namely the polyoxins and the nikkomycins. Each of these enzymatic inhibitors resembles the structure of the substrate, UDP-GlcNAc, and has inhibition constants ($K_i$) in the μM range (Decker et al., *J. Gen. Microbiol.*, 137:1805–1813

[1991]). Unfortunately, nikkomycin shows rapid degradation in biological fluids in rat, mouse and rabbit model systems (Tokumura and Horie, *Biol. Pharm. Bull.*, 20:577–580 [1977]).

Thus, there remains a need to identify new antimicrobial compounds, and more specifically, there is a need to identify and develop novel classes of antimicrobial compounds that have not been previously developed as antimicrobials, for the purpose of circumventing preexisting drug resistance and provides efficacious compounds to combat microbial disease. Indeed, there remains a need to identify and develop new classes of antimicrobial compounds that are effective against multiple-drug resistant organisms. In addition, there is a need to identify and develop antimicrobial compounds that demonstrate selective toxicity towards microorganisms, but are not toxic, or have minimal (i.e., tolerable) toxicity, to animal hosts (e.g., humans).

SUMMARY OF THE INVENTION

The present invention relates to methods to identify compounds having antimicrobial activity. These methods utilize a biochemical screen to identify antimicrobial compounds by testing the ability of the compound to inhibit the activity of microbial 2-amino-2-deoxy-D-glucose-6-phosphate ketol-isomerase (ketol-isomerase).

The present invention also relates to methods to identify compounds having antimicrobial activity that are likely to have no toxic effects, or minimal toxic effects, on the subject being treated for the microbial infection. These methods utilize a biochemical screen for ketol-isomerase activity using microbial ketol-isomerase enzymes, and also use ketol-isomerase enzymes from subjects that are to be treated for microbial infections to test whether the candidate compound inhibits the subjects' (i.e., the hosts') ketol-isomerase activity. Those compounds which inhibit microbial ketol-isomerase activity, but do not significantly inhibit the subjects' ketol-isomerase activity (i.e., preferentially inhibits the microbial ketol-isomerase) are candidates for development as antimicrobial drugs that have no or minimal toxicity to the subject being treated.

In one embodiment, the present invention provides methods for the detection of glutamate in an experimental sample, where the methods comprise the steps of providing an experimental sample, glutamate dehydrogenase, nicotinamide adenine dinucleotide, nitro blue tetrazolium chloride, and phenazine methosulfate; and combining these reagents with the sample under conditions where the nitro blue tetrazolium chloride is reduced to yield a chromogenic product, and the quantity of the chromogenic product produced is proportional to the amount of glutamate in the experimental sample. In a related embodiment, the present invention provides a method for quantitating the concentration of glutamate in the sample, where control samples containing known concentrations of glutamate are analyzed in parallel to the experimental sample, a standard curve is constructed using the control samples, and the glutamate concentration of the experimental sample is read from the standard curve.

In other embodiments, the present invention provides methods for the detection of ketol-isomerase activity in a sample, where the sample, fructose-6-phosphate, and glutamine are combined to produce glucosamine-6-phosphate and glutamate, the reaction is stopped, the glutamate is combined with glutamate dehydrogenase, nicotinamide adenine dinucleotide, nitro blue tetrazolium chloride, and phenazine methosulfate, where the nitro blue tetrazolium chloride is reduced to yield a chromogenic product, and the generation of the chromogenic product is proportional to the ketol-isomerase activity in the original sample.

In alternative embodiments of these methods, the sample being tested comprises fungal ketol-isomerases, bacterial ketol-isomerases, animal ketol-isomerases or plant ketol-isomerases. In other embodiments, the sample comprises a fungal cell lysate, a bacterial cell lysate, an animal cell lysate or a plant cell lysate. In alternative embodiments, the fungal cell lysate is from Aspergillus spp., Candida spp., Cryptococcus spp., Histoplasma spp., Pneumocystis spp., Rhizopus spp., Saccharomyces spp. (e.g., *S. cerevisiae*) or Schizosaccharomyces spp. (e.g., *S. pombe*). In other alternative embodiments, the bacterial cell lysate is selected from lysates of Escherichia spp. (e.g., *E. coli*), Staphylococcus spp. and Pseudomonas spp. In still other embodiments of these methods, the sample is a purified ketol-isomerase, while in other embodiments the sample is a recombinant ketol-isomerase. In one embodiment, the recombinant ketol-isomerase is a recombinant human ketol-isomerase.

In some embodiments of these methods for the detection of ketol-isomerase activity in a sample, the inactivation step for stopping the ketol-isomerase reaction which produces glutamate is accomplished by boiling, while in other embodiments, inactivation is by heating to 70° C. Furthermore, in other embodiments, after the inactivation step, the reaction can be clarified using either centrifugation, filtration or a combination of both techniques.

In one embodiment, the present invention provides a method for the identification of a compound having the ability to inhibit a microbial ketol-isomerase activity. In this embodiment, two reactions are prepared, where the first reaction comprises a microbial ketol-isomerase, fructose-6-phosphate and glutamine, and where the second reaction comprises a microbial ketol-isomerase, fructose-6-phosphate, glutamine and a candidate compound. In this embodiment, the reactions are run under conditions where the microbial ketol-isomerase produces glucosamine-6-phosphate and glutamate, the microbial ketol-isomerase reactions are then inactivated, the reaction mixtures are combined with glutamate dehydrogenase, nicotinamide adenine dinucleotide, nitro blue tetrazolium chloride, and phenazine methosulfate under conditions where the nitro blue tetrazolium chloride yields a chromogenic product, where the quantity of chromogenic product produced is proportional to microbial ketol-isomerase activity, and finally, comparing the ketol-isomerase activities in the first and second reaction mixtures, where if the ketol-isomerase activity of the first reaction mixture is greater than the ketol-isomerase activity of the second reaction mixture, the candidate compound has the ability to inhibit the microbial ketol-isomerase activity.

In alternative embodiments of these methods, the microbial ketol-isomerase comprises a crude fungal cell lysate, while in other embodiments, the microbial ketol-isomerase comprises a bacterial cell lysate. In alterantive embodiments, the fungal cell lysate is from Aspergillus spp., Candida spp., Cryptococcus spp., Histoplasma spp., Pneumocystis spp., Rhizopus spp., Saccharomyces spp. (e.g., *S. cerevisiae*) or Schizosaccharomyces spp. (e.g., *S. pombe*). In other alternative embodiments, the bacterial cell lysate is selected from lysates of Escherichia spp., (e.g., *E. coli*), Staphylococcus spp. and Pseudomonas spp.

In some embodiments of these methods for the detection of compounds that can inhibit ketol-isomerase activity, the inactivation step for stopping the ketol-isomerase reaction which produces glutamate is accomplished by boiling, while in other embodiments, inactivation is by heating to 70° C. Furthermore, in other embodiments, after the inactivation step, the reaction can be clarified using either centrifugation, filtration or a combination of both techniques.

In other embodiments of the present invention, a compound with the ability to inhibit a microbial ketol-isomerase activity is further tested for antimicrobial activity. In one embodiment, the method for testing for antimicrobial activity is an agar diffusion assay, while in another embodiment, the testing method is a broth dilution assay, while in another embodiment, the testing method is an in vivo mouse candidosis assay, and in yet another embodiment, the testing method is an in vivo mouse aspergillosis assay.

In other embodiments, the present invention provides methods for the identification of compounds that preferentially inhibit microbial ketol-isomerase rather than another (i.e., a second) ketol-isomerase. In this embodiment, third and fourth reaction mixtures are prepared, where the third reaction mixture comprises the other (i.e., second) ketol-isomerase, fructose-6-phosphate and glutamine, and where the fourth reaction mixture comprises the second ketol-isomerase, fructose-6-phosphate, glutamine and the candidate compound previously shown to inhibit microbial ketol-isomerase. In this embodiment, the third and fourth reaction mixtures are exposed to conditions where the second ketol-isomerase is capable of producing glucosamine-6-phosphate and glutamate, followed by inactivating the second ketol-isomerase, combining the third and fourth reaction mixtures with glutamate dehydrogenase activity, nicotinamide adenine dinucleotide, nitro blue tetrazolium chloride, and phenazine methosulfate under conditions where the nitro blue tetrazolium chloride is capable of producing a chromogenic product where the amount of chromogenic product produced is proportional to the amount of ketol-isomerase activity, and finally, comparing the microbial ketol-isomerase activities in the first and second reaction tubes, and comparing the second ketol-isomerase activities in the third and fourth reaction mixtures, and identifying a compound which preferentially inhibits the microbial ketol-isomerase activity compared to the second ketol-isomerase activity.

In some embodiments of this invention, the second ketol-isomerase is a plant ketol-isomerase, while in other embodiments, the second ketol-isomerase is an animal ketol-isomerase. In another embodiment, the animal ketol-isomerases are mammalian ketol-isomerases. In still further embodiments, the mammalian ketol-isomerases are rat ketol-isomerases, while in alternative embodiments, the mammalian ketol-isomerases are human ketol-isomerases.

In some embodiments, the second ketol-isomerase comprises a cell lysate. In some embodiments, the second ketol-isomerase is purified. In some embodiments, the second ketol-isomerase is a recombinant ketol-isomerase. In other embodiments, the recombinant ketol-isomerase is a recombinant human ketol-isomerase.

In some embodiments of these methods for the identification of compounds that preferentially inhibit microbial ketol-isomerase activity, the inactivation step for stopping the ketol-isomerase reaction which produces glutamate is accomplished by boiling, while in other embodiments, inactivation is by heating to 70° C. Furthermore, in other embodiments, after the inactivation step, the reaction can be clarified using either centrifugation, filtration or a combination of both techniques.

In other embodiments, where a compound preferentially inhibits a microbial ketol-isomerase activity compared to a second ketol-isomerase activity, that compound is further tested for antimicrobial activity using a testing means. In some embodiments, the means for testing antimicrobial activity is an agar diffusion assay, while in another embodiment, the testing method is a broth dilution assay, while in another embodiment, the testing method is an in vivo mouse candidosis assay, and in yet another embodiment, the testing method is an in vivo mouse aspergillosis assay.

DEFINITIONS

Figure 1:
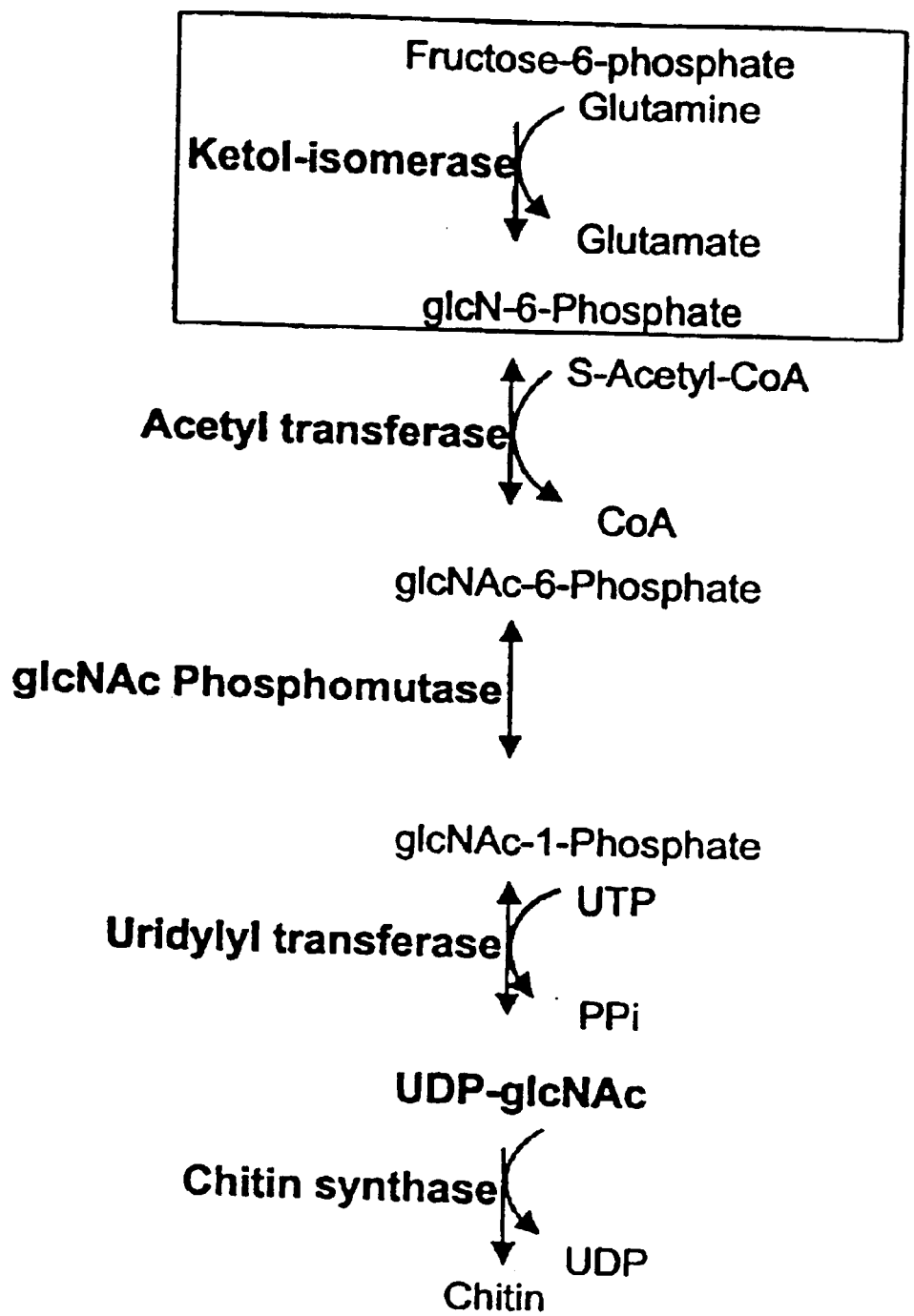
FIG. 1 shows the Leloir enzymatic pathway for the synthesis of the chitin precursor UDP-N-acetylglucosamine (UDP-GlcNAc). The chitin synthase step is also indicated, although this step is not formally part of the Leloir Pathway.

To facilitate understanding of the invention, a number of terms are defined and discussed below.

The terms "nucleic acid," "nucleic acid sequence," "nucleotide sequence," "oligonucleotide," "polynucleotide" or "nucleic acid molecule" as used herein refer to an oligonucleotide or polynucleotide, and fragments or portions thereof, and to DNA or RNA of genomic or synthetic origin which can be single- or double-stranded, and represent the sense or antisense strand. Similarly, "amino acid sequence" as used herein refers to the primary sequence of amino acids in a peptide, polypeptide or protein.

The term "nucleotide" as used herein refers to any nucleotide that comprises any of the known base analogs of DNA and RNA.

As used herein, "recombinant nucleic acid," "recombinant gene" "recombinant DNA molecule" or similar terms indicate that the nucleotide sequence or arrangement of its parts is not a native configuration, and has been manipulated by molecular biological techniques. The term implies that the DNA molecule is comprised of segments of DNA that have been artificially joined together. Protocols and reagents to manipulate nucleic acids are common and routine in the art (See e.g., Maniatis et al.(eds.), *Molecular Cloning: A Laboratory Manual*, Cold Spring Harbor Laboratory Press, N.Y., [1982]; Sambrook et al. (eds.), *Molecular Cloning: A*

*Laboratory Manual*, Second Edition, Volumes 1–3, Cold Spring Harbor Laboratory Press, N.Y., [1989]; and Ausubel et al. (eds.), *Current Protocols in Molecular Biology*, Vol. 1–4, John Wiley & Sons, Inc., New York [1994]).

As used herein, the terms "restriction endonucleases" and "restriction enzymes" refer to bacterial enzymes, each of which cut double-stranded DNA at or near a specific nucleotide sequence.

The term "homology," as it applies to nucleotide sequences, refers to a degree of complementarity. It is intended that the term encompass partial homology as well as complete homology (i.e., 100% identity). A partially complementary sequence is one that at least partially inhibits a completely complementary sequence from hybridizing to a target nucleic acid, and is referred to using the functional term "substantially homologous." The inhibition of hybridization of the completely complementary sequence to the target sequence can be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding, the probe will not hybridize to the second non-complementary target.

The terms "peptide," "polypeptide" and "protein" all refer to a primary sequence of amino acids that are joined by covalent "peptide linkages." In general, a peptide consists of a few amino acids, typically from 2–25 amino acids, and is shorter than a protein. "Polypeptides" encompass both peptides or proteins. As used herein, a recited "amino acid sequence" refers to an amino acid sequence of a naturally occurring protein molecule, a protein produced by recombinant molecular genetic techniques, or a synthetic or naturally occurring peptide, and may refer to a portion of a larger "peptide," "polypeptide" or "protein," and is not meant to limit the amino acid sequence to the complete, native amino acid sequence associated with the recited protein molecule.

A "recombinant protein" or "recombinant polypeptide" refers to a protein molecule that is expressed from a recombinant DNA molecule. Use of these terms indicates that the primary amino acid sequence, arrangement of its domains or nucleic acid elements which control its expression are not native, and have been manipulated by molecular biology techniques. As indicated above, techniques to manipulate recombinant proteins are also common and routine in the art.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" gene is a gene that does not contain nucleic acid elements encoded by sources other than the chromosome on which it is normally found in nature. An endogenous gene or transcript is encoded by its natural chromosomal locus, and not artificially supplied to the cell.

As used herein the term "portion" when in reference to a protein (as in "a portion of a given protein") refers to fragments of that protein. In some embodiments, the fragments range in size from four amino acid residues to the entire amino acid sequence minus one amino acid. In other embodiments, the "portion" is further limited to only fragments of the full length protein that retain biological activity. For example, a portion of a ketol-isomerase protein is a fragment of a ketol-isomerase protein that retains the ability to catalyze the synthesis of glucosamine-6-phosphate and glutamate from fructose-6-phosphate and glutamine. Functional portions of the ketol-isomerase protein find use with the present invention.

The following definitions are the commonly accepted definitions of the terms "identity," "similarity" and "homology." Percent identity, as it applies to polypeptides, is a measure of strict amino acid conservation. Percent similarity is a measure of amino acid conservation which incorporates both strictly conserved amino acids, as well as "conservative" amino acid substitutions, where one amino acid is substituted for a different amino acid having similar chemical properties (i.e., a "conservative" substitution). In some embodiments, the term "homology" pertains to either proteins or nucleic acids. Two proteins be described as "homologous" or "non-homologous," but the degree of amino acid conservation is quantitated by percent identity and percent similarity. Nucleic acid conservation is measured by the strict conservation of the bases adenine, thymine, guanine and cytosine in the primary nucleotide sequence. When describing nucleic acid conservation, conservation of the nucleic acid primary sequence is sometimes expressed as percent homology. In the same nucleic acid, one region may show a high percentage of nucleotide sequence conservation, while a different region shows no or poor conservation. It is not possible to infer nucleotide sequence conservation from an amino acid similarity score. Indeed, it is possible for two proteins to show domains that in one region are homologous, while other regions of the same protein the domains are non-homologous.

The term "isolated" when used in relation to a nucleic acid, as in "an isolated nucleic acid," "an isolated oligonucleotide," "isolated polynucleotide" or "isolated nucleotide sequence," refers to a nucleic acid that is identified and separated from at least one contaminant nucleic acid with which it is ordinarily associated in its natural source. Isolated nucleic acid is present in a form or setting that is different from the form or setting of that nucleic acid found in nature. In contrast, non-isolated nucleic acids are found in the state in which they exist in nature. For example, a given DNA sequence (e.g., a gene) is found on the host cell chromosome in proximity to neighboring genes; RNA sequences, such as a specific mRNA sequence encoding a specific protein, are found in the cell in a mixture with numerous other mRNAs that encode a multitude of proteins. However, isolated nucleic acid encoding a given polypeptide includes, by way of example, such nucleic acid in cells ordinarily expressing the given protein where the nucleic acid is in a chromosomal location different from that of natural cells, or is otherwise flanked by a different nucleic acid sequence than that found in nature. This isolated nucleic acid, oligonucleotide, or polynucleotide is either single-stranded or double-stranded. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide is single-stranded). In other embodiments, the oligonucleotide or polynucleotide contains both the sense and anti-sense strands (i.e., the oligonucleotide or polynucleotide is double-stranded).

As used herein, the terms "purified," "to purify" or "enriched" refer to the removal of at least one contaminant from a sample. As used herein, the term "substantially purified" refers to molecules, either nucleic acids or amino acid sequences, that are removed from their natural environment, "isolated" or "separated," and are largely free from other components with which they are naturally associated. An "isolated nucleic acid" or "isolated polypeptide" are therefore a substantially purified nucleic acid or substantially purified polypeptide. For example, antibodies are purified by removal of contaminating non-immunoglobulin proteins; they are also purified by the removal of non-specific immunoglobulin that does not bind to the target molecule. The removal of non-immunoglobulin proteins and/or the removal of immunoglobulins that do not bind to the target molecule results in an increase in the percent of target-reactive immunoglobulins in the sample. The removal of non-immunoglobulin proteins and/or the removal of immunoglobulins that do not bind to the target molecule results in an increase in the percent of target-reactive immunoglobulins in the sample (i.e., "enrichment" of an antibody). In another example, recombinant polypeptides are expressed in bacterial host cells and the polypeptides are purified by the removal of host cell proteins; the percent of recombinant polypeptides relative to all polypeptides in the sample is thereby increased.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also can be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, in some embodiments, enhancer elements exert their effect even when located 3' of the promoter element or the coding region. Transcription termination and polyadenylation signals are located 3' or downstream of the coding region.

The term "gene" refers to a nucleic acid (e.g., DNA) sequence comprised of parts, that when appropriately combined in either a native or recombinant manner, provide some product or function. In some embodiments, genes comprise coding sequences necessary for the production of a polypeptide, while in other embodiments, the genes do not comprise coding sequences necessary for the production of a polypeptide. Examples of genes that do not encode polypeptide sequences include ribosomal RNA genes (rRNA) and transfer RNA (tRNA) genes. In preferred embodiments, genes encode a polypeptide or any portion of a polypeptide within the gene's "coding region" or "open reading frame." In some embodiments, the polypeptide produced by the open reading frame of a gene displays functional activity or properties of the full-length polypeptide (e.g., enzymatic activity, ligand binding, signal transduction, etc.), while in other embodiments, it does not.

In addition to the coding region of the nucleic acid, the term "gene" also encompasses the transcribed nucleotide sequences of the full-length mRNA adjacent to the 5' and 3' ends of the coding region. These noncoding regions are variable in size, and typically extend for distances up to or exceeding 1 kb on both the 5' and 3' ends of the coding region. The sequences that are located 5' and 3' of the coding region and are contained on the mRNA are referred to as 5' and 3' untranslated sequences (5' UT and 3' UT). Both the 5' and 3' UT may serve regulatory roles, including translation initiation, post-transcriptional cleavage and polyadenylation. The term "gene" encompasses mRNA, cDNA and genomic forms of a gene.

In some embodiments, the genomic form or genomic clone of a gene contains the sequences of the transcribed mRNA, as well as other non-coding sequences which lie outside of the mRNA. The regulatory regions which lie outside the mRNA transcription unit are sometimes called "5' or 3' flanking sequences." A functional genomic form of a gene must contain regulatory elements necessary for the regulation of transcription. The term "promoter/enhancer region" is usually used to describe this DNA region, typically but not necessarily 5' of the site of transcription initiation, sufficient to confer appropriate transcriptional regulation. Used alone, the term "promoter" is sometimes used synonymously with "promoter/enhancer." In some embodiments, the promoter is constitutively active, or while in alternative embodiments, the promoter is conditionally active (i.e., where transcription is initiated only under certain physiological conditions or in the presence of certain drugs). In some embodiments, the 3' flanking region contains additional sequences which regulate transcription, especially the termination of transcription. "Introns" or "intervening regions" or "intervening sequences" are segments of a gene which are contained in the primary transcript (i.e., heteronuclear RNA, or hnRNA), but are spliced out to yield the processed mRNA form. In some embodiments, introns contain transcriptional regulatory elements such as enhancers. The mRNA produced from the genomic copy of a gene is translated in the presence of ribosomes to yield the primary amino acid sequence of the polypeptide.

As used herein, the term "regulatory element" refers to a genetic element which controls some aspect of the expression of nucleic acid sequences. For example, a promoter is a regulatory element that enables the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 [1987]). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review see, Voss et al.,

*Trends Biochem. Sci.,* 11:287 [1986] and Maniatis et al., *Science* 236:1237 [*1987*]). For example, the SV40 early gene enhancer is very active in a wide variety of mammalian cell types (Dijkema et al., *EMBO J.,* 4:761 [1985]). Two other examples of promoter/enhancer elements active in a broad range of mammalian cell types are those from the human elongation factor 1α gene (Uetsuki et al., *J. Biol. Chem.,* 264:5791 [1989]; Kim et al., *Gene* 91:217 [1990]; Mizushima and Nagata, *Nuc. Acids. Res.,* 18:5322 [1990]), the long terminal repeats of the Rous sarcoma virus (Gorman et al., *Proc. Natl. Acad. Sci. USA* 79:6777 [1982]), and human cytomegalovirus (Boshart et al., *Cell* 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. In some embodiments, the promoter/enhancer is "endogenous," while in other embodiments, the promoter/enhancer is "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

The terms "in operable combination," "in operable order," "operably linked" and similar phrases when used in reference to nucleic acid herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). In some embodiments, the coding region is present in a cDNA, while in other embodiments, the coding region is present in genomic DNA or RNA form. When present in a DNA form, the oligonucleotide, polynucleotide or nucleic acid is either single-stranded (i.e., the sense strand or the antisense strand) or double-stranded. In some embodiments, suitable control elements such as enhancers/promoters, splice junctions, polyadenylation signals, etc. are placed in close proximity to the coding region of the gene if needed to permit proper initiation of transcription and/or correct processing of the primary RNA transcript. Alternatively, the coding region utilized in the expression vectors of the present invention contains endogenous enhancers/promoters, splice junctions, intervening sequences, polyadenylation signals, etc. or a combination of both endogenous and exogenous control elements.

As used herein, the terms "nucleic acid molecule encoding," "DNA sequence encoding," and "DNA encoding" and similar phrases refer to the order or sequence of deoxyribonucleotides along a strand of deoxyribonucleic acid encoding a particular polypeptide. The order of the deoxyribonucleotides determines the order of the amino acids in the polypeptide chain. The DNA sequence thus codes for the amino acid sequence.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression regulation often occurs at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the term "vector" is used in reference to nucleic acid molecules that transfer DNA segment(s) from one cell to another. The term "vehicle" is sometimes used interchangeably with "vector." In some embodiments, a vector "backbone" comprises those parts of the vector which mediate its maintenance and enable its intended use (e.g., the vector backbone contains sequences necessary for replication, genes imparting drug or antibiotic resistance, a multiple cloning site, and possibly operably linked promoter/enhancer elements which enable the expression of a cloned nucleic acid). The cloned nucleic acid (e.g., such as a cDNA coding sequence, or an amplified PCR product) is inserted into the vector backbone using common molecular biology techniques. Vectors are often derived from plasmids, bacteriophages, or plant or animal viruses. A "cloning vector" or "shuttle vector" or "subcloning vector" contain operably linked parts which facilitate subcloning steps (e.g., a multiple cloning site containing multiple restriction endonuclease sites). A "recombinant vector" indicates that the nucleotide sequence or arrangement of its parts is not a native configuration, and has been manipulated by molecular biological techniques. The term implies that the vector is comprised of segments of DNA that have been artificially joined.

The term "expression vector" as used herein refers to a recombinant DNA molecule containing a desired coding sequence and operably linked nucleic acid sequences necessary for the expression of the operably linked coding sequence in a particular host organism (e.g., a bacterial expression vector, a yeast expression vector or a mammalian expression vector). Nucleic acid sequences necessary for expression in prokaryotes typically include a promoter, an operator (optional), and a ribosome binding site, often along with other sequences. Eukaryotic cells utilize promoters, enhancers, and termination and polyadenylation signals and other sequences which are different from those used by prokaryotes.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and in some embodiments, include gene sequences found in that animal so long as the introduced gene does not reside in the same location as does the naturally-occurring gene.

The terms "overexpression" and "overexpressing" and grammatical equivalents are used in reference to levels of mRNA or protein where the level of expression of the mRNA or protein is higher than that typically observed in a given cell (prokaryotic or eukaryotic) or in a tissue in a control or non-transgenic animal. Levels of mRNA or protein are measured using any of a number of techniques known to those skilled in the art. For example, in some embodiments mRNA levels are assayed using methods such as Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample is used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into cells. Transfection can be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Mammalian cell transfection techniques are common in the art, and are described in many sources (See, e.g., Ausubel et al. (eds.), *Current Protocols in Molecular Biology*, Vol. 1–4, John Wiley & Sons, Inc., New York [1994]).

The term "stable transfection" or "stably transfected" refers to the introduction and integration of foreign DNA into the genome of the transfected cell. The term "stable transfectant" refers to a cell which contains stably integrated foreign DNA within its own genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a eukaryotic cell, and most typically mammalian cells. The uptake of nucleic acids by cells is enhanced when the nucleic acid is presented as a calcium phosphate-nucleic acid co-precipitate. Various modifications of the original technique of Graham and van der Eb (Graham and van der Eb, *Virol.*, 52:456 [1973]) are known in which the conditions for the transfection of a particular cell type has been optimized. The art is well aware of these various methods.

The term "transformation" has various meanings, depending on its usage. In one sense, the term "transformation" is used to describe the process of introduction of foreign DNA into prokaryotic cells (i.e., bacterial cells), and most frequently *E. coli* strains. Bacterial cell transformation can be accomplished by a variety of means well known in the art, including the preparation of "competent" bacteria by the use of calcium chloride, magnesium chloride or rubidium chloride, and electroporation. When a plasmid is used as the transformation vector, the plasmid typically contains a gene conferring drug resistance, such as the genes encoding ampicillin, tetracycline or kanamycin resistance. Bacterial transformation techniques are common in the art, and are described in many sources (e.g., Cohen et al., *Proc. Natl. Acad. Sci. USA* 69:2110–2114 [1972]; Hanahan, *J. Mol. Biol.*, 166:557–580 [1983]; Sambrook et al. (eds.), *Molecular Cloning: A Laboratory Manual*, Second Edition, Volumes 1–3, Cold Spring Harbor Laboratory Press, NY, [1989]; Ausubel et al. (eds.), *Current Protocols in Molecular Biology*, Vol. 1–4, John Wiley & Sons, Inc., New York [1994]). "Transformation" also describes the physiological process by which a normal eukaryotic cell acquires the phenotypic qualities of a malignant cell. Such properties include, but are not limited to the ability to grow in soft agar, the ability to grow in nutrient poor conditions, rapid proliferation, and the loss of contact inhibition. A eukaryotic cell which is "transformed" displays the properties of malignant cells. In some embodiments, eukaryotic cells acquire their transformed phenotype in vivo, while in other embodiments, the cells are artificially transformed in culture.

As used herein, the term "selectable marker" refers to the use of a gene that encodes an enzymatic activity that confers the ability to grow in medium lacking what would otherwise be an essential nutrient; in other embodiments, a selectable marker, when expressed within a cell, confers resistance to an antibiotic or drug (e.g., the gene encoding the protein which confers resistance to ampicillin when expressed in a bacterial cells). Furthermore, some selectable markers are "dominant." Dominant selectable markers encode an enzymatic activity that is detectable in any suitable eukaryotic cell line. Examples of dominant selectable markers include the bacterial aminoglycoside 3' phosphotransferase gene (i.e., the neo gene) that confers resistance to the drug G-418 in mammalian cells, as well as the bacterial hygromycin G phosphotransferase (hyg) gene that confers resistance to the antibiotic hygromycin, and the bacterial xanthine-guanine phosphoribosyl transferase gene (i.e., the gpt gene) that confers the ability to grow in the presence of mycophenolic acid. The use of non-dominant selectable markers must be in conjunction with a cell line that lacks the relevant enzyme activity. Examples of non-dominant selectable markers include the thymidine kinase (tk) gene (used in conjunction with tk$^-$ cell lines), the CAD gene (used in conjunction with CAD-deficient cells) and the mammalian hypoxanthine-guanine phosphoribosyl transferase (hprt) gene (used in conjunction with hprt$^-$ cell lines). A review of the use of selectable markers in mammalian cell lines is provided in Sambrook et al., *Molecular Cloning: A Laboratory Manual*, Second Edition, Cold Spring Harbor Laboratory Press, New York (1989), at pp. 16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "transformant" refers to organisms and/or cells capable of harboring an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a transformant. In some embodiments, the transformant also transcribes and/or translates and expresses a gene contained on the exogenous nucleic acid. It is intended that the exogenous nucleic acid be obtained from any suitable source. In some embodiments, it is produced synthetically, while in other embodiments, it is produced by another cell or organism, and can be recombinant or non-recombinant. In addition, in some embodiments, the exogenous nucleic acid undergoes replication, while in other embodiments, it is not. For example, the bacterium *Escherichia coli* strain XL-1 Blue is suitable for use as a transformant for a bacterial expression vector encoding a ketolisomerase polypeptide.

As used herein, the term "prokaryote" refers to organisms distinguishable from "eukaryotes." It is intended that the term prokaryote encompass organisms that exhibit the characteristics indicative of prokaryotes, such as possessing a single, circular chromosome, the lack of a true nucleus, the lack of membrane-bound organelles, and other molecular characteristics indicative of prokaryotes. The term prokaryotes, as used herein, is synonymous with "bacteria" (i.e., eubacteria, excluding the archaebacteria).

As used herein, the term "eukaryote" refers to organisms distinguishable from "prokaryotes." It is intended that the term eukaryote encompass all organisms with cells that exhibit the usual characteristics of eukaryotes such as the presence of a true nucleus bounded by a nuclear membrane within which reside the chromosomes, the presence of membrane-bound organelles, and other characteristics commonly observed in eukaryotic organisms. Thus, the term eukaryotes includes, but is not limited to, such organisms as fungi (e.g., molds, sac fungi, club fungi, yeasts), multicellular photosynthetic plants (e.g., corn, wheat, barley, soybean, potato, lettuce, rice, tobacco and alfalfa), protozoa (e.g., Acanthamoeba spp., Trypanosoma spp., Leishmania spp., Plasmodium spp., Toxoplasma spp., Giardia spp.), and animals (e.g., humans, cattle, sheep, goats, pigs, chickens, turkeys, dogs, cats, horses, reptiles).

The term "sample" as used herein is used in its broadest sense, and can refer to a sample of biological or non-biological origin. A sample of biological origin refers to any type of material obtained from animals or plants (e.g., any fluid or tissue), cultured cells or tissues, cultures of microorganisms (prokaryotic or eukaryotic), and any fraction or products produced from a living (or once living) culture. A sample may be a cell extract (i.e., a crude lysate) or contain intact cells. The molecule of interest in a sample can be purified or unpurified (i.e., crude). An "experimental sample" is a sample where the presence, concentration and/or activity of some molecule of interest is unknown. A "control sample" is a sample where the presence, concentration and/or activity of some molecule of interest is known. For example, control samples containing known concentrations of some molecule of interest (e.g., glutamate), can be used to determine the concentration of glutamate in an experimental sample by using an indicator assay (e.g., the nitro BT assay) to construct a standard concentration curve. As used herein, a sample "suspected of containing" a component or biological/biochemical activity is a sample where the presence of the component or activity has not been demonstrated or proven.

As used herein, a "drug" can be any molecule of any composition, including protein, peptide, nucleic acid, organic molecule, inorganic molecule, or combinations of molecules, biological or non-biological, which are capable of producing a physiological response. As used herein, a "drug" provides at least one beneficial response in the cure, mitigation, treatment or prevention of a disease, condition or disorder (e.g., to treat a microbial infection). A compound is considered a "drug candidate" if it is not yet known if that compound will provide at least one beneficial response in the cure, mitigation, treatment or prevention of a disease, disorder or condition.

As used herein, the term "in vitro" refers to an artificial environment and to processes or reactions that occur within an artificial environment. The term "in vivo" refers to the natural environment (e.g., in an animal or in a cell) and to processes or reactions that occur within a natural environment. The definition of an in vitro versus in vivo system is particular for the system under study. For example, as used herein, assays for determining antifungal activity using the agar diffusion method is an in vitro assay system. Conversely, the determination of antifungal activity using a whole mouse candidiasis/candidosis model is an in vivo assay system.

As used herein, the term "subject" refers to any animal or plant being examined, studied or treated. It is not intended that the present invention be limited to any particular type of subject. It is contemplated that multiple organisms will find use in the present invention as subjects. In some embodiments of the present invention, humans are the preferred subject. Other animals may also be subjects, including but not limited to cattle, sheep, goats, pigs, chicken, turkeys, dogs, cats, horses and reptiles). In other embodiments, plants are the subjects for treatment (e.g., corn, wheat, barley, soybean, potato, lettuce, rice, tobacco and alfalfa).

As used herein, the term "inhibit" refers to the act of diminishing, suppressing, alleviating, preventing, reducing or eliminating. The term "suppress" may be used interchangeably with "inhibit." For example, a compound which inhibits microbial growth may completely cure (kill all microbial cells, i.e., bacteriocidal or fungicidal action), prevent microbial growth, arrest or slow further microbial growth (i.e., bacteriostatic or fungistatic action). The term "inhibit" can also be used to describe the effect of a compound on an enzymatic activity. Thus, the term "inhibit" as it applies to the analysis of enzymatic activity encompasses a range of effects, from completely eliminating to partially reducing. The term "inhibit" can be applied to both in vitro as well as in vivo systems.

As used herein, the term "bacteriocidal" refers to an agent that kills bacteria. However, a bacteriocidal agent is not necessarily able to kill bacterial spores. As used herein, the term "fungicidal" refers to an agent that kills fungi.

As used herein, the terms "bacteriostatic" and "fungistatic" refer to agents which slow or arrest the growth of bacteria and fungi, respectively, but do not kill the organism.

As used herein, the terms "local" and "localized" and the like refer to confinement to a small area or a single tissue (e.g., a small area on the skin). The term "localized delivery" is delivery of an agent (e.g., an antimicrobial compound) to a small area or single tissue. Localized delivery of an antimicrobial agent to the skin is termed "topical" delivery. A microbial infection may be "localized," (i.e., the infection is confined to a relatively small area or a single tissue, such as the skin), or may be "systemic" (i.e., the infection has spread to multiple sites, tissues or organs in a subject, typically via the circulatory or lymphatic systems). Similarly, delivery of an antimicrobial agent can be topical (e.g., where delivery is to the surface of the skin), or systemic (e.g., where delivery is by the circulatory system via an intravenous or intraarterial injection, or by gastrointestinal absorption if taken by mouth).

As used herein, the term "systemic" refers to multiple sites, tissues or organs in an organism, or to the entire organism. Use of the word "systemic" generally indicates involvement of the circulatory and/or lymphatic systems.

As used herein, the term "systemic delivery" (in contrast to localized delivery) involves delivery of an agent (e.g., a drug) to multiple sites, tissues or organs in an organism, or to the entire organism via the circulatory system following an intravenous injection, or via gastrointestinal absorption of an orally administered agent.

As used herein, the terms "antimicrobial," "antimicrobial chemotherapeutic," "antimicrobial drug," "antimicrobial compound" and "antimicrobial activity," are used in reference to any compound, substance or agent that inhibits the growth of microorganisms, including eukaryotic microorganisms (e.g., fungi) and prokaryotes (e.g., bacteria). Thus, antimicrobial agents comprise both antifungal and antibacterial agents. It is intended that the term be used in its broadest sense, and includes, but is not limited to, compounds that exist naturally (e.g., antibiotics) or compounds that are produced by artificial means (i.e., by in vitro chemical synthesis). Antimicrobials can be used with or on a subject in the treatment of microbial disease, infection, colonization or other pathology. Antimicrobials include compounds that kill or eliminate microbial growth as well as compounds that merely suppress, slow or arrest microbial growth. Antimicrobial activity can take place in vitro, as well as in vivo.

As used herein, the terms "antifungal," "antifungal agent," "antifungal chemotherapeutic," and "antifungal drug" refer to any compound, substance or agent used in the treatment of fungal condition, disease, infection or colonization. It includes fungicidal as well as fungistatic compounds which act on fungi in vitro, as well as in vivo. Examples of antifungal agents include amphotericin B, nystatin, fluconazole, itraconazole, naftifine, ketoconazole, 5-fluorocytosine and griseofulvin. The antifungals of the present invention are not limited to any particular mechanism of action. Nor is an understanding of the mechanism of action necessary to use the antifungals of the present invention.

Examples of fungal conditions, diseases and infections includes, but is not limited to: adiaspiromycosis, aspergillosis, dermatophytoses, blastomycosis, candidemia, cercosporamycosis, systemic and superficial candidiasis (i.e., candidosis), chromoblastomycosis, chromomycosis, coccidioidomycosis, cryptococcosis, cryptomycosis, dermatomycosis, entomophthoramycosis, favus (tinea favosa), fusariosis, geotrichosis, histoplasmosis, hyalohyphomycosis, lobomycosis, maduramycosis (Madura foot), mycetoma, mucormycosis, mycotic keratitis, mycotic keratosis, onychomycosis, oomycosis, otomycosis, paracoccidiomycosis, penicillosis, phaeohyphomycosis, phaeomycotic cyst, piedras (black piedra, white piedra), pityriasis nigra, pityriasis versicolor (i.e., tinea versicolor), pneumonia, protothecosis, rhinosporidiosis, ringworm, sporotrichosis, systemic mycoses, tinea, torulopsosis, trichomycosis axillaris, and zygomycosis. These examples are intended to be exemplary only, and it is not intended that the present invention be limited in scope by these examples.

As used herein, the terms "antibacterial," "antibacterial agent," "antibacterial chemotherapeutic," and "antibacterial drug" refer to any compound, substance or agent used in the treatment of bacterial condition, disease, infection or colonization. The term includes antibacterial activity that occurs in vitro, as well as in vivo. Antibiotics are antibacterial agents derived from natural sources (e.g., penicillin produced by the mold Penicillum). Examples of other antibacterial agents include erythromycin, tetracycline, rifampin, chloramphenicol, isoniazid, ampicillin, cephalosporin, gentamycin, kanamycin and tobramycin. The antibacterials of the present invention are not limited to any particular mechanism of action. Nor is an understanding of the mechanism of action necessary to use the antibacterials of the present invention.

Examples of bacterial conditions, diseases and infections includes, but is not limited to: anthrax, botulism, conjunctivitis, diphtheria, food poisoning, gastroenteritis, gonorrhea, meningitis, pneumonia, salmonellosis, shigellosis, skin and wound infections, syphilis, tetanus, tuberculosis, typhus and whooping cough. These examples are intended to be exemplary only, and it is not intended that the present invention be limited in scope by these examples.

As used herein, the term "antimetabolite" refers to any substance with a close structural resemblance to another essential substance (i.e., a metabolite) that is required for normal physiologic function. Typically, antimetabolites exert growth inhibitory effects by interfering with the utilization of the metabolite. For example, 5-fluorocytosine is an antimetabolite with antifungal activity, and sulfanilamide and isoniazid are antimetabolite antibacterials.

As used herein, the term "toxicity" generally refers to deleterious, impairing or injurious effects caused by a compound on a cell or organism. Toxicity can display a range of severity from mild to severe. In the extreme, severe toxicity causes the death of a cell or organism, where mild toxicity may result in symptoms in an organism that do not significantly impact the fitness or well-being of the organism.

As used herein, "selective toxicity" refers to the phenomenon where a compound may have toxic effects in one organism or cell type, but does not have those effects on a second organism or cell type, or has fewer or milder toxic effects on a second organism or cell type compared to the first organism or cell type. For example, most antibacterial compounds (e.g., penicillin) are effective in treating infections in a subject because of the selective toxicity displayed by the antibacterial compound, where the antibacterial compound demonstrates severe toxicity towards the bacteria in a bacterial infection in a host (i.e., bacteriocidal activity), but that compound does not show toxicity towards the subject being treated for the infection (e.g., a human). Selective toxicity may be relative (i.e., not absolute). For example, a compound that demonstrates potent antibacterial activity may also have mild toxic effects (i.e., tolerable, manageable or minimal effects) on the host subject (e.g., a human) being treated for the infection. If the mild toxicity experienced by the subject does not significantly impact the fitness or long-term well-being of the host organism, such toxicity may be acceptable in the treatment of the infection.

As used herein, the term "ketol-isomerase activity" refers to that enzymatic activity catalyzed by the ketol-isomerase enzyme. Ketol-isomerase activity is that activity that catalyzes the formation of glucosamine-6-phosphate (GlcN-6-P) and glutamate (Glu) from fructose-6-phosphate (Fru-6-P) and glutamine (Gln) (See, FIG. 1). The presence of ketol-isomerase activity in a sample is indicative of the presence of the ketol-isomerase enzyme (i.e., "ketol-isomerase" in that sample. However, the absence of ketol-isomerase activity in a sample does not imply the absence of ketol-isomerase enzyme, as the presence of an inhibitor may suppress the ketol-isomerase activity, although the enzyme is present. As used herein, the addition, identification or detection of ketol-isomerase activity implies the presence of ketol-isomerase enzyme.

DESCRIPTION OF THE INVENTION

The present invention provides novel and improved methods for the assay of ketol-isomerase activity. In particularly preferred embodiments, the present invention provides methods that utilize the redox-sensitive chromophore nitro blue tetrazolium chloride (nitro BT). The present invention further provides methods for drug screening to identify compounds that have the ability to suppress microbial ketol-isomerase activity. It is contemplated that compounds that inhibit microbial ketol-isomerase activity also have antimicrobial activity, and can be used to treat microbial infections (e.g., fungal and/or bacterial infections). The present invention also provides methods for the identification of antimicrobial compounds that have selective inhibit microbial ketol-isomerase compared to a subject's (e.g., mammalian) ketol-isomerase activity. Although an understanding of the mechanism by which a compound inhibits ketol-isomerase activity is not necessary in order to make or use the present invention, the structure, function and regulation of this enzyme are described below. Similarly, an understanding of the mechanism by which a compound imparts antimicrobial activity is not necessary in order to make or use the present invention. In addition, it is not intended that the present invention be limited to any particular mechanisms of antimicrobial action and/or ketol-isomerase activity inhibition.

Ketol-Isomerase

The enzyme ketol-isomerase (2-amino-2-deoxy-D-glucose-6-phosphate ketol-isomerase; E.C. 2.6.1.16 or E.C. 5.3.1.19) is required for the biosynthesis of chitin, as well as other macromolecules. The enzyme is also known as glutamine:fructose-6-phosphate amidotransferase or glucosamine-6-phosphate synthase. The enzyme catalyzes the formation of glucosamine-6-phosphate (GlcN-6-P) and glutamate (Glu) from fructose-6-phosphate (Fru-6-P) and glutamine (Gln) (See, FIG. 1).

Ketol-isomerase activity has been identified and characterized in humans (McKnight et al., *J. Biol. Chem.*, 267:25208–25212 [1992]; and Daniels et al., *J. Clinical Invest.*, 97(5):1235–1241 [1996]), other mammals (Winterburn and Phelps, *Biochem. J.*, 121:701–709 [1971]; and Zalkin *Methods Enzymol.*, 113:278–281 [1985]), plants, fungi (Endo et al., *J. Bacteriol.*, 103:588–594 [1970]; Smith et al., *J. Bacteriol.*, 178:2320–2327 [1996]; Watzele and Tanner, *J. Biol. Chem.*, 264:8753–8758 [1989]; Borgia, *J. Bacteriol.*, 174:384–389 [1992]; Milewski et al., *J. Biol. Chem.*, 274(7):4000–4008 [1999]; and Etchebehere and Da Costa Maia, *Arch. Biochem. Biophys.*, 272:301–310 [1989]), and bacteria (Kornfeld, *J. Biol. Chem.*, 242:3135 [1967]; and Badet et al., *Biochemistry* 26:1940–1948 [1987]). Significant biochemical distinctions can be made between these ketol-isomerase orthologs. For example, the bacterial enzyme is not inhibited by the end-product of the Leloir Pathway, UDP-N-acetylglucosamine (UDP-GlcNAc; See, FIG. 1; Endo et al., *J. Bacteriol.*, 103:588–594 [1970]). However, ketol-isomerase activity from both fungal and mammalian sources is feedback-inhibited by UDP-GlcNAc (Endo et al., *J. Bacteriol.*, 103:588–594 [1970]). Another important distinction between fungal and mammalian ketol-isomerases can be made, in that sensitivity of the fungal enzyme to UDP-GlcNAc is dependent on the phosphorylation state of the ketol-isomerase (i.e., the enzyme is only feedback-inhibited when it is phosphorylated). In contrast, phosphorylation does not play a role in mammalian ketol-isomerase regulation (McKnight et al., *J. Biol. Chem.*, 267:25208–25212 [*1992*]; and Selitrennikoff et al., *Proc. Natl. Acad. Sci. USA* 77:5998–6002 [1980]). Also, the fungal enzyme appears to be a homodimer of a 76 kDa subunit, while the human enzyme appears to be in the range of 340–360 kDa (a homotetramer of an ~80 kDa subunit), and the bacterial enzyme is monomeric (McKnight et al., *J. Biol. Chem.*, 267:25208–25212 [1992]). Representative ketol-isomerases have been cloned and sequenced and the amino acid alignments of the predicted proteins have shown that while there are regions of conserved amino acids, there are also regions of significant sequence divergence between human, bacterial and fungal ketol-isomerases (Smith et al., *J. Bacteriol.*, 178:2320–2327 [1996]).

The enzymatic product of ketol-isomerase, GlcN-6-P, is a precursor of UDP-N-acetyl glucosamine (UDP-GlcNAc), which itself is the major intermediate of numerous macromolecules including glycoproteins, proteoglycans, and glycolipids in mammals, chitin and mannoproteins in fungi, and peptidoglycan and lipopolysaccharides in bacteria. It is known that mutations that inhibit ketol-isomerase activity result in the inhibition of fungal growth (Katz and Rosenberger, *Biochim. Biophys. Acta*, 208:452–560 [1970]; and Russell and Srb, *Molec. Gene. Genet.*, 129:77–86 [1974]). Furthermore, compounds that inhibit fungal ketol-isomerase activity also inhibit *C. albicans* growth (Milewski et al., *Antimicrob. Agents Chemo.*, 35:36–43 [1991]; and Milewski et al., *Drugs Exp. Clin. Res.*, 14(7):461–465 [1988]).

Taken together, these results indicate that ketol-isomerase activity is required for fungal growth, the structure of fungal and mammalian ketol-isomerases are different, and microbial and mammalian ketol-isomerases are regulated through different mechanisms. Thus, selective inhibitors of fungal ketol-isomerase activity, which have little or no effect on mammalian ketol-isomerase activity, can be identified. Therefore, such compounds are a potential target for the development of antifungal and antibacterial agents. Furthermore, the lack of chitin in mammalian cells makes their biosynthesis pathways attractive targets for antifungal compounds. However, the use of compounds that selectively inhibit microbial ketol-isomerase activity as antimicrobial agents does not require an understanding of the mechanism by which the compound functions in order to make and use the present invention. Nor is it intended that the present invention be limited to any particular mechanism.

Ketol-Isomerase Activity Assays

Methods to determine ketol-isomerase enzymatic activity have been previously reported. Some of these methods quantitate GlcN-6-P, one of the products of the ketol-isomerase reaction. These methods include the Morgan-Elson assay (Zalkin, *Methods Enzymol.*, 113:278–281 [1985]), a spectrophotometric assay (Badet et al., *Biochemistry* 26:1940–1948 [1987]), and high performance liquid chromatography (HPLC) procedure (Daniels et al., *J. Clin. Invest.*, 97:1235–1241 [1996]). However, none of these methods are amendable for high throughput screening, as they require steps that are not easily automated (e.g., repeated boiling steps), incorporate toxic reagents (e.g., hydrochloric acid and acetic acid anhydrate), require chemically unstable reagents (e.g., acetic acid anhydride) and/or require specialized equipment (HPLC apparatus). For example, automation of the Morgan-Elson assay is hampered by multiple boiling steps and the requirement for 10 N hydrochloric acid, measurement of UV absorption is needed in the spectrophotometric assay, and HPLC is an equipment-intensive and expensive methodology.

An alternative method for the quantitation of ketol-isomerase activity in crude cell lysate has also been described which measures the concentration of glutamate, a ketol-isomerase reaction by-product, and uses p-iodonitrotetrazolium violet (Selitrennikoff and Ostroff, *Emerging Therapeutic Targets* 3:53–72 [1999]). This iodonitrotetrazolium violet assay uses a two step enzymatic method requiring glutamate dehydrogenase (E.C. 1.4.1.3) and diaphorase (E.C. 1.8.1.4). In this assay, glutamate dehydrogenase first converts glutamate to α-ketoglutarate, utilizing the oxidized form of nicotinamide adenine dinucleotide (β-NAD) as a cofactor. In the second step of the assay, the enzyme diaphorase reduces p-iodonitrotetrazolium violet (INV), using β-NADH (the reduced form of β-NAD produced from the prior enzymatic step). The compound p-iodonitrotetrazolium violet is a chromophore that reflects red light following its reduction by β-NADH. The amount of light produced by the chromophore (measured spectrophotometrically) following exposure to β-NADH is proportional to the amount of glutamate present following the ketol-isomerase reaction.

In this iodonitrotetrazolium violet assay, two exogenous enzymes (glutamate dehydrogenase and diaphorase) are required. Therefore, not only ketol-isomerase inhibitors, but also inhibitors of these exogenous enzymes are detected by this assay, thus, "false positives" are detected. Furthermore, since two enzymatic reactions are required in this method, the assay is subject to an added component of variability. Therefore, establishment of a ketol-isomerase assay that is amenable to high-throughput automation (e.g., using microtiter plates), yields minimal false positive results and shows minimal variability is needed in the art to provide a tool for screening antimicrobial agents.

The Nitro BT Ketol-Isomerase Assay of the Invention

Figure 2:
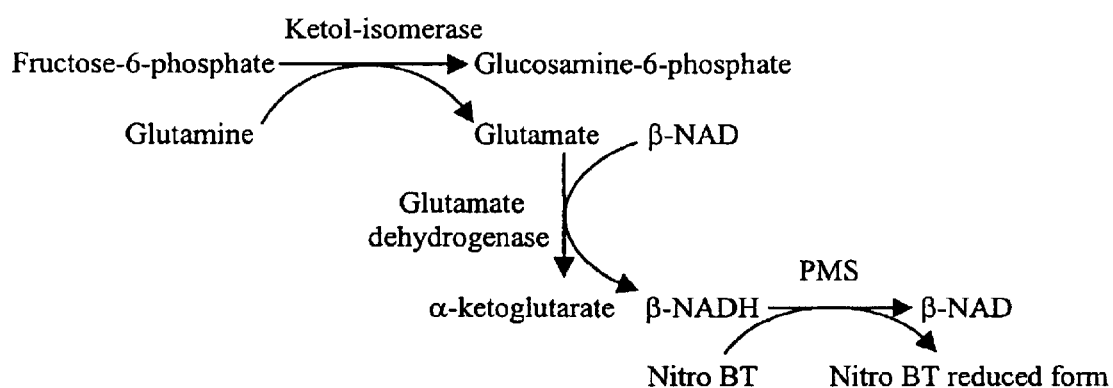
FIG. 2 shows the ketol-isomerase/glutamate dehydrogenase/nitro BT assay reaction steps.

The present invention provides simplified and improved methods for the assay (i.e., quantitation) of ketol-isomerase activity by indirectly determining glutamate concentration. As shown in FIG. 2, GlcN-6-P and glutamate are produced as products of the ketol-isomerase reaction. The ketol-isomerase reaction is followed by a heat inactivation step, resulting in the irreversible denaturation of the enzyme and permanent cessation of further ketol-isomerase activity. Following the heat inactivation step, a secondary enzymatic reaction is employed with glutamate dehydrogenase to produce α-ketoglutarate and β-NADH from the glutamate (produced in the ketol-isomerase reaction) and a molar excess of β-NAD. The β-NADH produced in this secondary reaction is then quantitated using a redox-sensitive chromogenic substrate.

The reduction-sensitive chromophore used in this method is nitro blue tetrazolium chloride (nitro BT). Nitro BT is reduced in the presence of β-NADH and phenazine methosulfate (PMS) to yield a compound that is measurable at a 585 nm wavelength, and is readily quantitated using standard colorimetric spectrophotometry (Van Noorden and Butcher, *Anal. Biochem.*, 176:170–174 [1989]). A schematic of this reaction is shown in FIG. 2. The use of nitro BT to indirectly measure ketol-isomerase enzymatic activity by quantitating the accumulation of the secondary reaction product (β-NADH) is novel. The nitro BT assay is applicable to the assay of ketol-isomerase activity from any organism, and as shown below, is equally or more sensitive than known ketol-isomerase activity assays. Furthermore, in the nitro BT assay, only one supplemental enzymatic reaction is used in the assay (i.e., the glutamate dehydrogenase reaction). Thus, the number of false positives and interassay variability are reduced.

The nitro BT assay method was first tested to determine whether the assay provided a linear response using known glutamate concentration standards. The detailed conditions of this experiment are described in Example 1. Briefly, aliquots of glutamate standard solutions ranging in concentration from 0 to 600 μM were placed in the wells of a 96 well microtiter plate and combined with the reaction buffer containing glutamate dehydrogenase enzyme and molar excesses of NAD, PMS, and nitro BT. The mixture was incubated for 15 min at room temperature, followed by spectrophotometric analysis at 585 nm.

Figure 3:
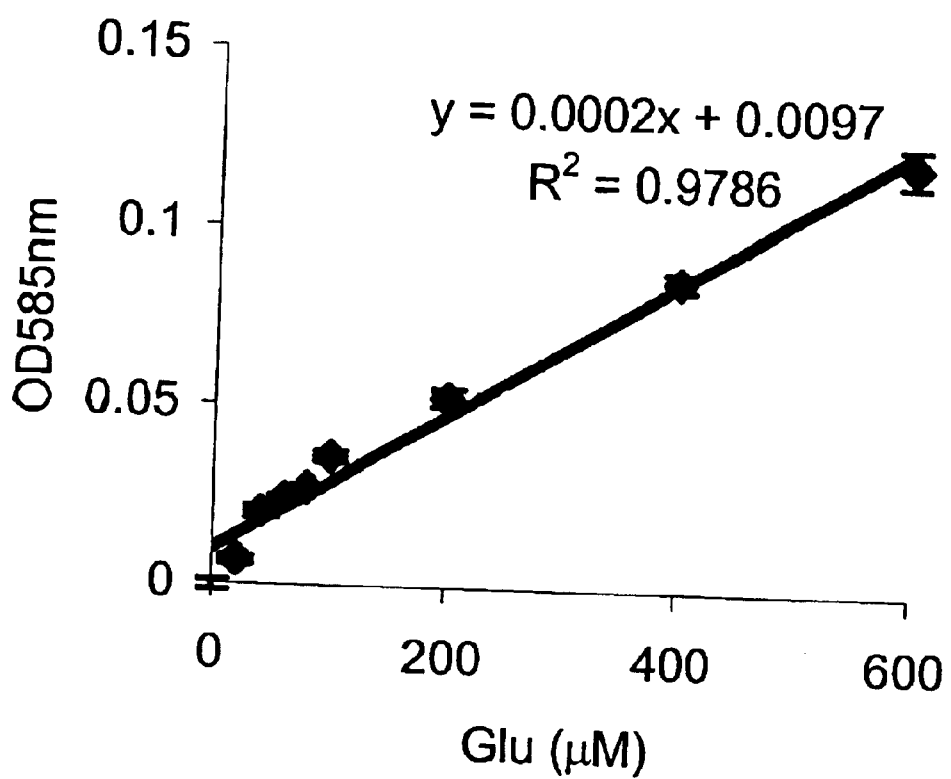
FIG. 3 shows a standardization plot for glutamate (Glu) concentration using the nitro blue tetrazolium chloride (nitro BT) assay, where the glutamate concentration ranges from 0 to 600 $\mu$M.

The results of this experiment are shown in FIG. 3, where the plot depicts the $OD_{585\ nm}$ as a function of glutamate standard concentration. Each data point indicates the mean $OD_{585\ nm}$ of triplicate samples±the standard deviation (S.D.). As indicated in FIG. 3, glutamate concentrations within this range yielded a linear response with respect to the calorimetric detection of the reduced form of the nitro BT. This indicates a direct correlation between glutamate concentration and optical density, thus verifying that OD is an appropriate measure of glutamate concentration following the glutamate dehydrogenase and nitro BT reactions.

Side-By-Side Comparison of Nitro BT and Morgan-Elson Assays

Following verification of the nitro BT assay to quantitate glutamate, suitability of the assay to quantitate ketol-isomerase activity was addressed in a side-by-side comparison with the Morgan-Elson assay to quantitate glutamate and GlcN-6-P concentrations, respectively, following a ketol-isomerase reaction. The source of the ketol-isomerase activity was a crude cell extract prepared from *Aspergillus fumigatus* hyphae. The specific experimental conditions used in this comparison are provided in Examples 1, 4 and 5.

Briefly, to prepare the cell extract, *A. fumigatus* conidia were used to inoculate a liquid culture and incubated. Hyphae were harvested by vacuum filtration, washed, snap-frozen, and stored at −80° C. until use. The frozen *A. fumigatus* hyphae were thawed and disrupted by bead-beating using 0.5 mm zirconium beads in physiological sucrose buffer. The resulting lysates were centrifuged to remove cell debris, and supernatants were stored at −80° C. until ready for use in the ketol-isomerase assay.

Each ketol-isomerase reaction mixture contained 0.3 mg protein/mL of the cell lysate and molar excesses of fructose-6-phosphate (Fru-6-P) and glutamine. The reactions were incubated at 37° C. for 20, 40 or 60 minutes, and then were terminated by boiling for 5 minutes, or alternatively, by heating to 70° C. for 15 minutes. The reaction mixtures were then centrifuged, and the clarified supernatants were used in the Morgan-Elson and nitro BT assays.

As discussed above, the ketol-isomerase reaction catalyzes the formation of glucosamine-6-phosphate (GlcN-6-P) and glutamate (Glu) from fructose-6-phosphate (Fru-6-P) and glutamine (Gln) (as shown in FIG. 2). The two end products of this in vitro reaction, namely GlcN-6-P and glutamate, were quantitated using the Morgan-Elson and nitro BT assays, respectively.

A modified Morgan-Elson assay was used to determine GluN-6-P concentration following the ketol-isomerase reaction (as described in Example 4). Briefly, saturated $NaHCO_3$ solution and acetic acid were combined with the ketol-isomerase reaction supernatant. The mixture was incubated at room temperature for 3 minutes, boiled for 3 minutes, followed by the addition sodium borate solution, boiled again for 8 minutes, then finally cooled to room temperature. Ehrlich's reagent (See, Example 4) was then added to each reaction, followed by incubation at 37° C. for 20 minutes and colorimetric analysis ($OD_{585\ nm}$). In the Morgan-Elson assay, color development is directly proportional to GluN-6-P concentration. Samples of GluN-6-P of known concentration were analyzed in parallel to provide standardization values in order to determine absolute GluN-6-P concentration in the experimental samples.

Determination of glutamate concentrations was also done using the nitro BT assay of the present invention, as described above, and in Examples 1 and 5. In this experiment, samples of glutamate of known concentration were analyzed in parallel, to provide standardization values, in order to determine absolute glutamate concentration in the experimental samples.

Figure 4:
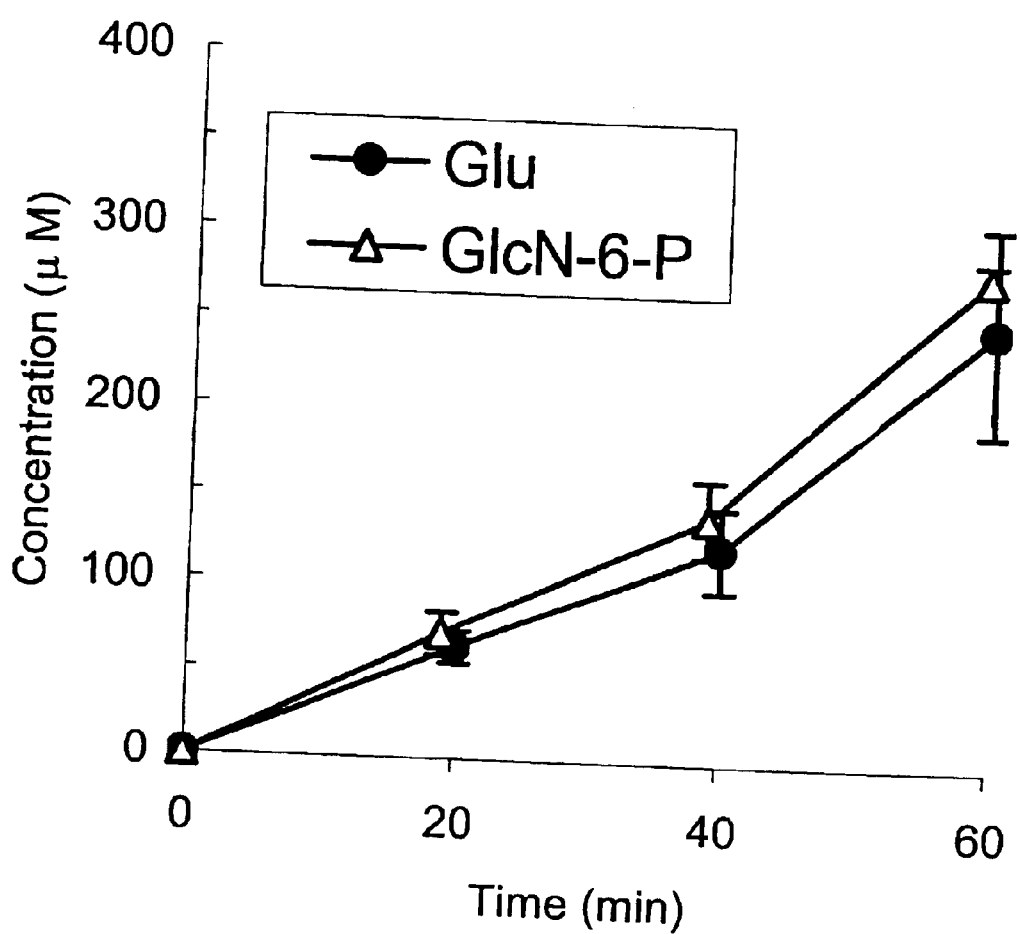
FIG. 4 shows two plots of ketol-isomerase activity of a crude *Aspergillus fumigatus* cell extract using two different assay methods. One plot provides results of the Morgan-Elson assay to determine the concentration of the ketol-isomerase reaction product glucosamine-6-phosphate (GlnN-6-P; open triangles). The second plot provides results of the nitro BT assay to determine the concentration of the ketol-isomerase reaction product glutamate (Glu; closed circles).

Finally, the GlcN-6-P and glutamate concentrations determined by the Morgan-Elson and nitro BT assays, respectively, were plotted on the same graph over the time course of the ketol-isomerase reaction. The results of this side-by-side comparison are shown in FIG. 4. If the Morgan-Elson and nitro BT assays are equally sensitive, it was predicted that the concentration curves for GlcN-6-P and glutamate during the ketol-isomerase reaction would be identical, since the GlcN-6-P and glutamate are produced by the ketol-isomerase reaction in a 1:1 stoichiometric ratio. As indicated in FIG. 4, these two different methods yielded nearly identical concentrations of these two reaction products. In a control ketol-isomerase reaction that omitted glutamine, neither glutamate nor GlcN-6-P were detected (data not shown).

From these results, it is clear that the nitro BT assay of the present invention is able to quantitate ketol-isomerase activity at least as effectively as the Morgan-Elson assay. In addition, the present invention provides advantages over current methods for the identification of inhibitors of ketol-isomerase, as the methods of the present invention have fewer and simplified steps compared to those known in the art (e.g., the Morgan-Elson assay).

Detection of Inhibitors of Ketol-Isomerase Using the Nitro BT Assay

It is contemplated that compounds that inhibit microbial ketol-isomerase activity will find use as antimicrobials suitable for use in treatment of microbial infections and disease. It is further contemplated that the nitro BT assay of the present invention will find widespread use in the identification of compounds that have the ability to inhibit the activity of fungal or bacterial ketol-isomerase. Furthermore, the nitro BT assay of the present invention is readily adapted for use in high throughput drug screening. In addition, the present invention provides methods for the identification of undeveloped and/or unknown antimicrobial agents. Also, use of the antimicrobial drugs identified using the methods of the present invention are less likely to be subject to microbial resistance.

In order to demonstrate the ability of the nitro BT assay to detect compounds having the ability to suppress ketol-isomerase activity, a known inhibitor of ketol-isomerase was included in an *A. fumigatus* ketol-isomerase reaction assay, as described in Example 6. In this experiment, UDP-N-acetylglucosamine (UDP-GlcNAc) was added to the ketol-isomerase reaction at a concentration range from 0 to 10 mM. UDP-GlcNAc is known to cause feedback inhibition of *Neurospora crassa* ketol-isomerase (Endo et al., *J. Bacteriol.*, 103:588–594 [1970]).

Briefly, in this experiment, a series of ketol-isomerase reactions were analyzed in parallel, wherein each reaction mixture contained Fru-6-P, glutamine, and crude *A. fumigatus* cell extract (as described in Example 3). In addition, reactions also contained various concentrations of UDP-GlcNAc, ranging from 0 to 10 mM. Reactions were incubated at 37° C. for 60 minutes, after which time the ketol-isomerase reactions were terminated by heating at 70° C. for 15 min. However, the ketol-isomerase reaction can also be terminated by boiling for 5 minutes. In addition, the ketol-isomerase reaction can be clarified following the inactivation step by centrifugation or filtration.

Following arrest of the ketol-isomerase reaction, the necessary reagents for the nitro BT reaction were added to each reaction mixture, including glutamate dehydrogenase enzyme and molar excesses of β-NAD, PMS, and nitro BT. After incubation at 37° C. for 90 minutes, the color development was quantitated by measurement of $OD_{585\ nm}$.

Figure 5:
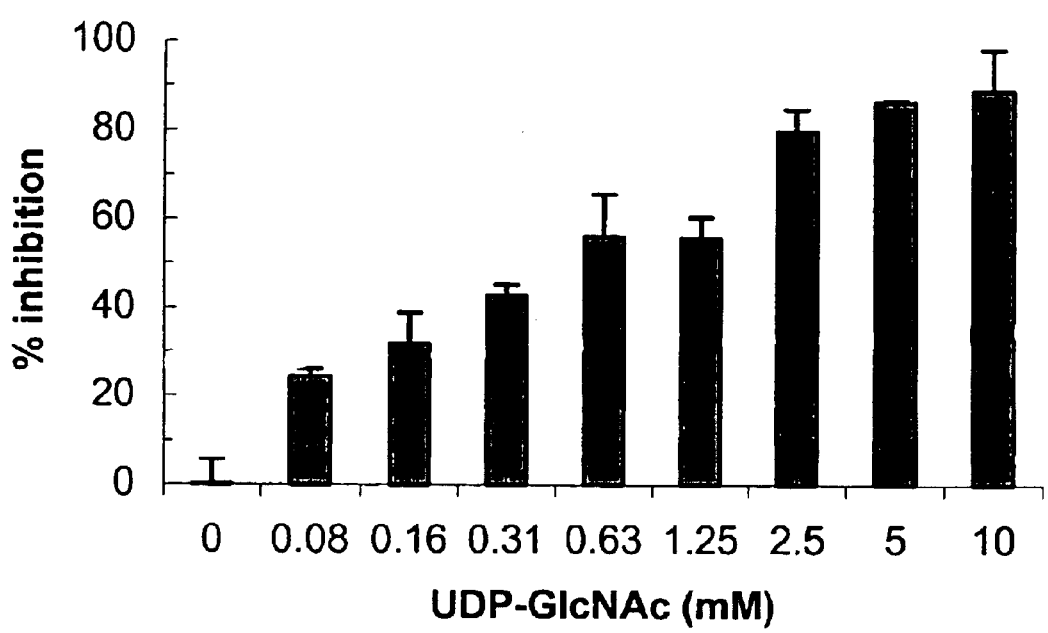
FIG. 5 provides a histogram plot showing the ability of UDP-N-acetylglucosamine (UDP-GlcNAc) to inhibit the activity of ketol-isomerase (feedback inhibition) from a crude *A. fumigatus* cell extract, as measured by the nitro BT assay, where the UDP-GlcNAc concentration ranges from 0 to 10 mM.

The results of this assay are shown in a bar-graph format in FIG. 5. Each data point represents the mean of three samples; the standard deviation of each data point is indicated by a vertical line. As indicated in FIG. 5, the ketol-isomerase activity contained in the *A. fumigatus* crude extract was inhibited by UDP-GlcNAc in a dose-dependent manner. The $IC_{50}$ (concentration of a compound which inhibits enzymatic activity to 50% relative to an untreated control) was 0.48 mM. This inhibitory effect is similar to that previously observed with UDP-GlcNAc in the inhibition of ketol-isomerase activity from *C. albicans* strain ATCC No. 10261 crude cell extracts ($IC_{50}$=0.69 mM; Milewski et al., *J. Biol. Chem.*, 274:4000–4008 [1999]). These results indicate that ketol-isomerase inhibitors can be successfully detected using the nitro BT assay of the present invention.

Although the present invention was reduced to practice using crude cell lysates from the fungus *A. fumigatus* as a source of ketol-isomerase activity, it is not intended that the invention be limited to this particular fungal species. Indeed, the present invention finds use with crude cell lysates of numerous fungal species, especially pathogenic fungal species. In addition, non-pathogenic fungal species also find use with the present invention as a source of ketol-isomerase activity (e.g., *Saccharomyces cerevisiae* and *Schizosaccharomyces pombe*). Thus, the present invention encompasses use with various fungi, including but not limited to:

Absidia spp. (e.g., *A. corymbifera*),

Acremonium spp. (e.g., *A. falciforme, A. kiliense,* and *A. recifei*),

Aspergillus spp. (e.g., *A. flavus, A. fumigatus, A. niger, A. versicolor, A. nidulans, A. sydowii, A. terreus* and *A. flavipes*), Blastomyces spp. (e.g., *B. dermatitidis*), Candida spp. (e.g., *C. albicans, C. tropicalis, C. kefyr, C. guilliermondii, C. krusei* and *C. parapsilosis, C. glabrata, C. catenulata, C. ciferrii, C. haemulonii, C. lipolytica, C. lusitaniae, C. novegensis, C. pulcherrima, C. rugosa, C. utilis, C. viswanathii* and *C. zeylanoides*),

*Cladosporium werneckii,*

*Claviceps purpura,*

Coccidioides immitis,

Cryptococcus spp. (e.g., *C. neoformans, C. albidus, C. laurentii, C. luteolus, C. terreus* and *C. uniguttulatus*), Epidermophyton spp. (e.g., *E. floccosum*), Fusarium spp., Histoplasma spp. (e.g., *H. capsulatum*), Microsporum spp., Mucor spp.,

*Paracoccidioides brasiliensis,*

*Philophora verrucosa,*

*Peidraia hortai,*

*Pityrosporum orbiculare,*

Pneumocystis spp. (e.g., *P. carinii*),

Rhizomucor spp. (e.g., *R. pusillus*),

Rhizopus spp. (e.g., *R. microsporus, R. arrhizus* and *R. oryzae*),

Saccharomyces spp. (e.g., *S. cerevisiae*),

Schizosaccharomyces spp. (e.g. *S. pombe*),

*Sporothrix schenckii,*

Trichophyton spp., and

*Trichosporon beigelii.*

Of the species in this list, Aspergillus spp., Candida spp., Cryptococcus spp., Histoplasma spp., Pneumocystis spp., Rhizopus spp., Saccharomyces spp. (e.g., *S. cerevisiae*) and Schizosaccharomyces spp. (e.g., *pombe*) find particular use with the invention. However, the above list is intended to be exemplary only, and is not intended to limit the scope of the invention, nor limit the sources of ketol-isomerase used with the present invention.

Furthermore, bacterial sources of ketol-isomerase activity also find use with the present invention. In one embodiment, bacterial extracts containing ketol-isomerase activity find use in identifying compounds that have the ability to suppress bacterial ketol-isomerase activity, and thus, can identify compounds with antibacterial activity. The preparation of suitable bacterial extracts are common in the art, and protocols to prepare such extracts can be found in numerous sources (See, e.g., Ausubel et al. (eds.), *Current Protocols in Molecular Biology*, "Analysis of Protein Interactions," p. 20.2.1–20.2.10, John Wiley & Sons, Inc., New York [1994]). In one such protocol, *Escherichia coli* can be grown overnight in 1.0 L LB liquid culture to generate starting material to prepare bacterial cell lysate. The cells are harvested by centrifugation, and the resulting pellet is washed with a buffer such as PBS or other physiological salt buffer (e.g., a buffer containing 50 mM potassium phosphate, 150 mM potassium chloride and 1 mM magnesium chloride, pH 7.5). After washing, the cells are pelleted again, and resuspended in 10 mL of the potassium phosphate buffer described above, and subjected to sonication using a microprobe for a series of 5×1 minute intervals. After the sonication, the cells are centrifuged to remove the cell debris, the supernatant is recovered, and the protein concentration of the resulting cell lysate is determined. The lysate can be optionally stored with glycerol, a detergent such as Triton X-100, and/or protease inhibitors. In preferred embodiments, lysates from pathogenic bacterial species are used (e.g., *Staphylococcus aureus* and *Pseudomonas aeruginosa*). It is not intended that the present invention be limited to the use of *E. coli* as a source of ketol-isomerase activity, as any other bacterial species that produces ketol-isomerase finds use with the present invention. For example, the present invention finds use with various bacterial species, including but not limited to:

Bacillus spp. (e.g., *B. anthracis*),

*Bordetella pertussis,*

Brucella spp.,

Campylobacter spp.,

Chlamydia spp.,

Clostridium spp.,

Enterococcus spp. (e.g., *E. faecalis, E. faecium, E. mundtii, E. hirae, E. casseliflavus* and *E. gallinarum*), Escherichia spp. (*E. coli*), Haemophilus spp. (e.g., *H. influenzae*), Helicobacter spp. (e.g., *H. pylori*), Klebsiella spp., Mycobacterium spp., Neisseria spp., Pseudomonas spp. (e.g., *P. aeruginosa, P. fluorescens, P. stutzeri, P. oryzihabitans, P. luteola, P. alcaligene* and *P. mendocina*), Rickettsia spp., Salmonella spp.,

*Serratia marcescens,*

Shigella spp.,

Staphylococcus spp. (e.g., *S. aureus, S. epidermitis, S. saprophyticus, S. haemolyticus, S. capitis, S. caprae, S. lugdunensis, S. saccharolyticus, S. simulans, S. warneri, S. hominis, S. schleiferi* and *S. intermedius*), Streptobacillus spp., Streptococcus spp. (e.g., *S. pyogenes, S. agalactiae, S. pneumoniae, S. sanguis, S. mitis, S. oralis, S. gordonii, S. intermidius, S. anginosus, S. salivarius* and *S. bovis*), Treponema spp., Vibrio spp., and Yersinia spp.

Of the species in this list, *Escherichia coli*, Staphylococcus spp. and Pseudomonas spp. find particular use with the invention. However, the above list is intended to be exemplary only, and is not intended to limit the scope of the invention, nor limit the sources of ketol-isomerase used with the present invention.

Furthermore, purified enzymatic preparations obtained using the methods of the present invention find use as a source of ketol-isomerase activity suitable for use in the ketol-isomerase reaction. Such preparations can be derived from any species (e.g., bacteria, fungi or animals), and the method of purification is not limited to any particular method. Indeed, numerous techniques are known in the art for polypeptide purification (e.g., ammonium sulfate precipitation, gel chromatography, ion exchange chromatography, affinity chromatography, etc.). These techniques may be used independently or in an appropriate combination to purify a ketol-isomerase polypeptide from a cell lysate starting culture.

In alternative embodiments, protocols employing molecular genetics techniques are used to overexpress a recombinant ketol-isomerase protein (derived from any species) in *E. coli*, followed by harvesting of the *E. coli* and preparation of a crude cell lysate for use in the ketol-isomerase reaction. Alternatively still, in some embodiments, the crude cell lysate collected from the *E. coli* overexpressing the recombinant ketol-isomerase protein is used as starting material for purification or enrichment of the protein, and that purified protein is suitable for use in the ketol-isomerase assay. In still other embodiments, fusion protein constructs are used to generate a recombinant chimeric protein, where the chimeric protein has a fused "tag" that facilitates purification of the protein. Examples of fusion protein methods include fusions with glutathione-S-transferase (GST), maltose binding protein (MBP), polyhistidine tags (i.e., 6×His), and thioredoxin tags. Numerous protocols for the purification of proteins, the use of bacterial overexpression systems, and construction of chimeric fusion proteins are widely known to those skilled in the art (See, e.g., Ausubel et al. [eds.], *Current Protocols in Molecular Biology*, Sections 10.9–10.11, and 16.1–16.8, John Wiley & Sons, Inc., New York [1994]). Furthermore, methods for the cloning, genetic manipulation and purification of ketol-isomerase enzyme from bacterial, fungal and mammalian species are also known (Badet et al., *Biochemistry* 26:1940–1948 [1987]; McKnight et al., *J. Biol. Chem.*, 267:25208–25212 [1992]; Milewski et al., *J. Biol. Chem.*, 274:4000–4008 [1999]; Smith et al., *J. Bacteriol.*, 178:2320–2327 [1996]; Watzele and Tanner, *J. Biol. Chem.*, 264:8753–8758 [1989]; Winterburn and Phelps, *Biochem. J.*, 121:701–709 [1971]; and Zalkin *Methods Enzymol.*, 113:278–281 [1985]).

Further still, it is not intended that the present invention be limited to the use of a full length ketol-isomerase protein in these enzymatic assay methods, as either full length or truncated ketol-isomerase proteins find use in these in vitro assays. However, when truncated enzymes are used in these assays, these enzymes must exhibit ketol-isomerase activity.

Thus, the drug screening methods provided by the present invention find use with crude cell extracts (i.e., lysates), as well as or purified protein fractions, and the source of the ketol-isomerase activity is not limited to any particular source. Therefor, ketol-isomerases of any species find use with the methods of the present invention, even though their respective ketol-isomerase proteins or genes have not been purified and/or isolated. It is not intended that the present invention be limited to any particular species as a source of ketol-isomerase activity, any particular method for preparing a cell lysate, nor any particular method for enzyme purification or enrichment, as those in the art will recognize numerous equivalent methods that find use with the present invention.

The present invention provides methods for the identification of compounds having the ability to inhibit microbial ketol-isomerase activity. Compounds having the ability to inhibit ketol-isomerase activity are candidates for further development as antimicrobial agents. In the methods provided by the present invention, a series of ketol-isomerase reactions are analyzed, where each ketol-isomerase reaction mixture contains Fru-6-P, glutamine, and a source of microbial ketol-isomerase (as described in Example 3). In addition, reactions also containing the test compound are analyzed in parallel. Reactions are incubated at 37° C. for 60 minutes, after which time the ketol-isomerase reactions are terminated, The conditions of 37° C. and 60 minutes are intended to be exemplary only, and are not intended to limit the methods of the present invention, as other conditions also find use with the invention. All reactions, including those reactions containing the test compound, are conducted under conditions where ketol-isomerase is capable of producing GlcN-6-P and glutamate (e.g., 37° C. for 60 minutes). In the event that the test compound is a strong inhibitor of ketol-isomerase activity, little or no GlcN-6-P and glutamate are produced, despite the fact that the reaction was conducted under conditions that would otherwise result in the formation of GlcN-6-P and glutamate.

Identification of Selectively Toxic Antimicrobial Compounds

In a most preferred embodiment, the present invention provides methods for identifying compounds that selectively inhibit microbial ketol-isomerase activity relative to mammalian ketol-isomerase activity. The compounds identified in these methods, thereby, are antimicrobial compounds that have no toxic effects on a host when administered to treat (i.e., eradicate, ameliorate or prevent) a microbial infection. In another embodiment, the antimicrobial compounds identified in the methods of the present invention display selective toxicity, in which the compound having potent antimicrobial activity has fewer or mild toxic effects (i.e., tolerable, manageable or minimal effects) on the host subject (e.g., a human) being treated for the infection. In this embodiment, the mild toxicity experienced by the subject being treated does not significantly impact the fitness or long-term well-being of the subject, and such toxicity may be acceptable in the treatment of the infection. In a most preferred embodiment, the subject is a human, although the antimicrobial compounds identified in these methods can be used to treat any subject, including but not limited to other mammalian and non-mammalian animals (e.g., cattle, sheep, goats, pigs, chickens, turkeys, dogs, cats, horses and reptiles) and plants (e.g., corn, wheat, barley, soybean, potato, lettuce, rice, tobacco and alfalfa).

Thus, the present invention provides methods for the identification of compounds having selective toxicity towards microbial species, but are not toxic or are less toxic (i.e., minimally toxic) towards the subject species (e.g., animals or plants). As described above, the nitro BT assay of the present invention finds use in the identification of compounds that inhibit microbial (e.g., bacterial or fungal) ketol-isomerase activity. In some embodiments, following the identification of such a compound, the compound is then tested in a ketol-isomerase activity assay using a second source of ketol-isomerase, to determine whether the compound has inhibitory activity towards the second ketol-isomerase, where the second source of ketol-isomerase is from a species that is a potential subject (e.g., a higher plant or animal). In a preferred embodiment, a compound that has inhibitory activity towards a microbial ketol-isomerase will have less or no inhibitory activity towards a subject's ketol-isomerase (i.e., the compound preferentially inhibits the microbial ketol-isomerase activity compared to the subject's ketol-isomerase activity). Thus, the present invention provides means to identify compounds that inhibit microbial ketol-isomerase(s), but do not inhibit or inhibit to a lesser extent a subject's ketol-isomerase(s), for use as antimicrobials, and have minimal or no toxicity when administered to a subject.

In preferred embodiments, a mammalian ketol-isomerase is used; however, it is not intended that the source of the mammalian ketol-isomerase be limited. In particularly preferred embodiments, the mammalian ketol-isomerase is a human ketol-isomerase. Furthermore, in most preferred embodiments, the source of human ketol-isomerase is a recombinant human ketol-isomerase expressed in host bacteria, and a crude cell extract (i.e., cell lysate) of that bacteria is used in the ketol isomerase assay. In other embodiments, the recombinant human ketol-isomerase in the bacterial cell extract is purified and/or enriched prior to use in the ketol-isomerase assay.

The cloning, purification and use of crude or purified mammalian ketol-isomerase preparations is known in the art (McKnight et al., *J. Biol. Chem.*, 267:25208–25212 [1992]; Daniels et al., *J. Clinical Invest.*, 97(5):1235–1241 [1996]; Winterburn and Phelps, *Biochem. J.*, 121:701–709 [1971]; and Zalkin *Methods Enzymol.*, 113:278–281 [1985]). In a particularly preferred embodiment of the present invention, a cloned human ketol-isomerase cDNA overexpressed in *E. coli*, which are used to produce a crude bacterial lysate containing human ketol-isomerase activity (as described in McKnight et al., *J. Biol. Chem.*, 267:25208–25212 [1992]) are used. In this protocol, the open reading frame encoding the human ketol-isomerase is subcloned into a vector (pPROK-1; Clontech) permitting inducible expression in bacterial cells (*E. coli* XL-1 Blue; Stratagene) via an operably linked tac promoter. The transformed bacteria are grown in liquid culture, and expression of the human ketol-isomerase is induced by the addition of isopropylthio-β-galactopyranoside (IPTG) for two hours. Cell pellets are harvested by centrifugation, then resuspended in lysis buffer (100 mM $NaH_2PO_4$ [pH 7.5], 50 mM KCl, 10 mM EDTA, 12 mM glucose-6-phosphate and 100 mM phenylmethylsulfonyl fluoride [PMSF]). Cells are lysed by sonication, and the crude cytosol is recovered by centrifugation. This crude lysate is used directly in the ketol-isomerase reaction (with and without the compound being tested), followed by the nitro BT assay to determine whether the compound has the ability to inhibit the human ketol-isomerase activity.

In an alternative embodiment, human ketol-isomerase activity is obtained by harvesting a crude lysate from cultured human cells (as described in Daniels et al., *J. Clinical Invest.*, 97(5):1235–1241 [1996]). In this protocol, human cells (e.g., primary myotubes from human muscle biopsy) are cultured, followed by harvesting, lysing by sonication, then centrifuging to obtain the crude human cell lysate containing ketol-isomerase activity.

In still another alternative embodiment of the present invention, a purified preparation of rat ketol-isomerase is used in the ketol-isomerase reaction (as described in Winterburn and Phelps, *Biochem. J.*, 121:701–709 [1971]; and Zalkin *Methods Enzymol.*, 113:278–281 [1985]). In this protocol, rat livers are obtained from sacrificed animals, and placed in a homogenization buffer (50 mM Tris, 5 mM EDTA, 5 mM glutathione, 5 mM glucose-6-phosphate, and 100 mM KCl, pH 7.8). The tissue is homogenized in a mechanical homogenizer, then followed by low-speed and high-speed centrifugation steps to remove cell debris. The supernatant is recovered, and subjected to two DEAE-cellulose column chromatography steps, and an hydroxyapatite fractionation. Ammonium sulphate fractionation may also be incorporated into the purification protocol. These methods of protein purification are described in many sources, and are known to those familiar with the art.

Assays for Antimicrobial Activity

In some embodiments, compounds identified as being capable of inhibiting microbial ketol-isomerase activity also have antimicrobial activity, and are suitable for use in the treatment of microbial infections. In one embodiment of the present invention, compounds able to inhibit microbial ketol-isomerase are tested for their ability to inhibit microbial growth. Inhibition of microbial growth can include the complete killing and elimination of microbial cells, the slowing of the rate of growth of microbial cells, or the arrest of microbial metabolism. Numerous methods are known in the art for the assessment of antimicrobial activity (See e.g., Turnidge and Jorgensen and Kennedy, Ch. 115, "Antimicrobial Susceptibility Testing: General Consideration," Jorgensen et al., Ch. 118, "Antibacterial Susceptibility Tests: Dilution and Disk Diffusion Methods," Ferraro and Jorgensen, Ch. 123, "Susceptibility Testing Instrumentation and Computerized Expert Systems for Data Analysis and Interpretation," Inderlied and Salfinger, Ch. 124, "Antimycobacterial Agents and Susceptibility Tests," and Espinel-Ingroff et al., Ch. 126, "Antifungal Agents and Susceptibility Tests," all in Murray et al., (eds), *Manual of Clinical Microbiology*, 7th ed., ASM Press, Washington, D.C. [1999]; and National Committee for Clinical Laboratory Standards [NCCLS], "Reference Method for Broth Dilution Susceptibility Testing of Yeasts, Publication M27-A [1997]). Thus, it is not intended that the present invention be limited to any particular method for screening for antimicrobial activity, as numerous antimicrobial activity assays find use with the present invention, as known to those familiar with the art.

In some embodiments of the present invention, compounds having the ability to inhibit bacterial ketol-isomerase activity are tested for antibacterial activity using in vitro assays. Methods to test the antibacterial activity of a compound are common in the art, and include dilution susceptibility assays (broth and agar methods), and agar diffusion assays (e.g., disk diffusion), (See e.g., National Committee for Clinical Laboratory Standards [NCCLS], "Methods for Dilution Antimicrobial Susceptibility Tests for Bacteria That Grow Aerobically," Publication M7-A4 [1997]; and Jorgensen et al., Ch. 118, p. 1526–1543, "Antibacterial Susceptibility Tests: Dilution and Disk Diffusion Methods," in Murray et al., (eds), *Manual of Clinical Microbiology*, 7th ed., ASM Press, Washington, D.C. [1999]). In some embodiments, these methods are adapted to provide for high throughput screening of large numbers of compounds. A variety of bacterial species find use in the in vitro antimicrobial testing methods. In some embodiments, known reference strains that are genetically stable are used in these methods, including but not limited to *E. coli* (e.g., ATCC Strain No. 25922), *S. aureus* (e.g., ATCC Strain) and *P. aeruginosa* (e.g., ATCC Strain No. 27853).

In other embodiments of the present invention, compounds having the ability to inhibit fungal ketol-isomerase activity are tested for antifungal activity using various in vitro assays. Methods to test the antifungal activity of a compound are common in the art, and include broth macrodilution and broth microdilution assays, agar diffusion assays (e.g., disk diffusion), and agar-dilution assays (See, e.g., National Committee for Clinical Laboratory Standards [NCCLS], "Reference Method for Broth Dilution Susceptibility Testing of Yeasts," Publication M27-A [1997]). In some embodiments, these methods are adapted to provide for high throughput screening of large numbers of compounds. In some embodiments, known reference strains of fungal species, including but not limited to Candida spp. (e.g., *C. parapsilosis* ATCC Strain No. 22019 and *C. krusei* ATCC Strain No. 6258) and Aspergillus spp. are used in in vitro testing.

In addition, it is not intended that the invention be limited to the use of any one particular microbial growth inhibition assay and/or antimicrobial testing method. Indeed, numerous methods find use with the present invention. Similarly, it is not intended that the present invention be limited to assays utilizing Candida spp., Aspergillus spp., *E. coli*, *S. aureus* or *P. aeruginosa*, as these species are only exemplary, and other microbial species also find use with the present invention.

In addition, in some preferred embodiments of the present invention, compounds which demonstrate an ability to inhibit microbial ketol-isomerase activity in vitro and have antimicrobial properties in vitro are tested in an in vivo animal models of disease. For example, in some preferred embodiments, the mouse model of candidosis/candidemia is used. This fungal infection model is known in the art (Hanson et al., *Antimicrob. Agents Chemother.*, 35:1334–1337 [1991]).

Briefly, two groups of five-week-old female CD-1 mice (Charles River Laboratories) are infected intravenously with a wild-type *C. albicans* strain. Concurrently, the mice in one of the groups are also injected with a test compound suspected of having antimicrobial activity (as determined in vitro). Mouse mortality is scored over 14 days post-infection. Alternatively, mice are injected with the test compound after an interval of time following the original inoculation with *C. albicans*. This alternative protocol allows the determination of whether a compound is capable of eliminating infection (i.e., as opposed to preventing the infection).

It is not intended that the invention be limited to the use of one particular in vivo infection model. It is contemplated that other in vivo infection assays will be used with the present invention. Indeed, it is contemplated that any method suitable to determine the in vivo effectiveness of an antimicrobial compound or combination of compounds will find use in the present invention. For example, a mouse model of aspergillosis using *A. fumigatus* finds use with the present invention. This method is known in the art, and uses a method nearly identical to that described above for the mouse candidemia model, with the exception that *A. fumigatus* is used as the mouse inoculum. It is also not intended that the present invention be limited to use in identifying compounds effective in the treatment of *C. albicans* or *A. fumigatus* infections, as the present invention provides methods suitable for the identification of antimicrobial compounds effective in the treatment of numerous microbial infections.

In some preferred embodiments of the present invention, candidate antimicrobial compounds advance through sequential screening steps in order to identify promising compounds for further clinical development. In particularly preferred embodiments, the identification of candidate therapeutic compounds is conducted in three sequential steps. It is contemplated that each step of this sequential screening will eliminate candidates from further development. These steps include:

1) Identification of compounds which inhibit a microbial ketol-isomerase activity in vitro;
2) Identification of those compounds identified in the first step which preferentially inhibit a microbial ketol-isomerase compared to a subject's (e.g., a mammalian) ketol-isomerase in vitro; and
3) Identification of compounds from the second step which have antimicrobial activity.

Optionally, candidate compounds may also be tested in an in vivo antimicrobial system, such as an in vivo mouse candidosis/candidiasis or aspergillosis model system and/or an in vivo bacterial infection model system. In some embodiments, these enzymatic assays, colorimetric quantitations, and antimicrobial assays described herein are automated to facilitate high throughput screening (e.g., the Biomek 2000 robot from Beckman Instruments, Inc.)

The present invention finds use in the identification of compounds (i.e., drugs) that have therapeutic value in eliminating, mitigating and/or preventing microbial infections and/or disease. Examples of conditions, diseases and disorders which can be treated using compounds identified using the methods of the present invention are listed herein. However, it is not intended that the present invention be limited to treating only those conditions, diseases and disorders listed herein, as the present invention finds use in the treatment of additional diseases, disorders or conditions. Similarly, it is not intended that the present invention be limited to the treatment of only those diseases, disorders or conditions caused by microbial species listed herein. Rather, the present invention also finds use in treating microbial pathology caused by organisms other than those specifically recited herein.

The present invention solves a need in the art for methods to identify new classes of compounds which have antimicrobial therapeutic activity against various pathogenic and opportunistic fungi and bacteria.

Experimental

The following Examples are provided in order to demonstrate and further illustrate certain preferred embodiments and aspects of the present invention and are not to be construed as limiting the scope thereof.

As used herein, the following scientific abbreviations/ notations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); mL (milliliters); $\mu$L (microliters); cm (centimeters); mm (millimeters); $\mu$m (micrometers); nm (nanometers); MW (molecular weight); ° C. (degrees Centigrade); OD (optical density); EDTA (ethylenediamine-tetracetic acid); SDS (sodium dodecyl sulfate); PAGE; UV (ultraviolet); $\mu$g/mL (microgram per milliliter); mm (millimeter); xg (times gravity); HPLC (high pressure liquid chromatography); DDT (dithiothreitol); PMSF (phenylmethylsulfonyl fluoride); SDS (sodium dodecyl sulfate); s and sec (seconds), m and min (minutes), h and hr (hours), w/v (weight to volume measure), v/v (volume to volume measure).

Restriction enzymes, other common molecular biology enzymes and reagents used in these experiments are widely available from numerous sources, including NEB, Promega, Fisher and Stratagene. Fungal and bacterial growth media (e.g., YG and LB, and agar-containing formulations of these media) are well known in the art and are available from suppliers such as Difco.

As used herein, the following abbreviations apply: ATCC (American Type Culture Collection, Manassas, Va.); Beckman Instruments, Inc. (Beckman Instruments, Inc., Fullerton, Calif.); Charles River Laboratories (Charles River Laboratories, Inc., Wilmington, Mass.); Clonetech (Clonetech, Palo Alto Calif.); DIFCO or Difco (Difco Laboratories, Detroit, Mich.); Fisher (Fisher Scientific, Pittsburgh, Pa.); Gibco-BRL or BRL or Life Technologies (GIBCO BRL Life Technologies, Gaithersburg, Md.); ICN (ICN Biochemicals, Inc., Costa Mesa, Calif.); Molecular Devices (Molecular Devices Corp., Sunnyvale, Calif.); Promega (Promega Corp., Madison, Wis.); Sigma (Sigma Chemical Company/Aldrich, St. Louis, Mo.); Stratagene (Stratagene, La Jolla, Calif.); and Whatman (Whatman, Inc., Clifton, N.J.).

EXAMPLE 1

Determination of Glutamate Concentration by the Nitro BT Assay

In this Example, experiments to determine the relationship between glutamate concentration and the reduced form of nitro BT using the nitro BT colorimetric assay of the present invention (See, FIG. 2) are described. In preliminary experiments, glutamine standard solutions of known concentration were tested.

Within the wells of a 96 well microtiter plate, 50 $\mu$L aliquots of glutamate standard solution (0, 20, 40, 60, 80, 100, 200, 400 or 600 $\mu$M glutamate) were combined with 50 $\mu$L of nitro BT reaction buffer (2 mM nicotinamide adenine dinucleotide, oxidized form [NAD; Sigma], 16 $\mu$M phenazine methosulfate [PMS; Sigma], 1 mM nitro blue tetrazolium chloride [NBT or nitro BT; Sigma, Catalog No. N-6876], and 5 units/mL glutamate dehydrogenase [Sigma, Catalog No. G-2501] in 100 mM potassium phosphate buffer ($KH_2PO_4$ and $K_2HPO_4$, pH 7.8). The mixture was incubated for 15 min at room temperature, followed by spectrophotometric (optical density, OD) analysis at 585 nm using a SPECTRAmax® 340 microplate reader (Molecular Devices Corp.).

The results of this experiment are shown in FIG. 3, in which the plot depicts $OD_{585\ nm}$ as a function of glutamate standard concentration, with glutamate concentrations ranging from 0 to 600 $\mu$M. Each data point indicates the mean $OD_{585\ nm}$ of triplicate samples±the standard deviation (S.D.). As can be seen in the Figure, glutamate concentrations within this range yielded a linear response with respect to the colorimetric detection (i.e., reduction) of nitro BT.

EXAMPLE 2

Preparation of *Aspergillus fumigatus* Crude Cell Lysate

In this Example, the growth, harvesting and preparation of *Aspergillus fumigatus* crude cell lysates are described. The resulting crude cell extract is used in the ketol-isomerase reaction, as described in Examples 3 and 6.

A. fumigatus ATCC16424 (a human clinical isolate) was inoculated into liquid YG medium (1% yeast extract [w/v] and 1% glucose [w/v]) with a final inoculum concentration of $1\times10^7$ conidia per/mL, and incubated for 20 hours at 37° C. with shaking (250 rpm). Hyphae were harvested by vacuum filtration over Whatman No.2 filter paper, washed twice with ice-cold water, quick-frozen in dry ice, and stored at −80° C. until use.

Frozen A. fumigatus hyphae were thawed and disrupted by bead-beating (6×30 seconds pulses with 2 minutes cooling between each pulse) using 0.5 mm zirconium beads in KI buffer (600 mM sucrose, 1 mM KCl, 1 mM EDTA and 50 mM PIPES, pH 6.8). The lysates were centrifuged at 1,000×g for 10 minutes at 4° C. The supernatants were recovered and stored at −80° C. and used as the source material for the ketol-isomerase assay.

EXAMPLE 3

Ketol-Isomerase Reaction

In this Example, a source of fungal ketol-isomerase activity was used to catalyze the formation of glucosamine-6-phosphate (GlcN-6-P) and glutamate (Glu) from fructose-6-phosphate (Fru-6-P) and glutamine (Gln). The end products of this in vitro reaction were assayed using the quantitation methods described in Example 4 (i.e., the Morgan-Elson assay) and Example 1 (i.e., the nitro BT assay). A direct comparison of these two methods was then made (See, Example 5 and FIG. 4).

The ketol-isomerase enzymatic reaction was conducted in a total final volume of 100 $\mu$L, which contained 10 mM Fru-6-P (Sigma), 10 mM Gln (ICN) and 0.3 mg protein/mL of crude *Aspergillus fumigatus* (ATCC No. 16424) cell extract prepared as described in Example 2. The reaction was incubated at 37° C. for 0, 20, 40 or 60 minutes. The reaction was terminated by boiling for 5 minutes, followed by centrifugation at 10,000×g. The supernatant was recovered and used in the Morgan-Elson and nitro BT quantitation assays. The ketol isomerase reaction, as well as the quantitative Morgan-Elson and nitro BT assays were performed in triplicate to ensure reproducibility.

EXAMPLE 4

Morgan-Elson Assay

In this Example, a modified Morgan-Elson assay used to quantitate the concentration of glucosamine-6-phosphate (GlcN-6-P) in a sample following the ketol-isomerase reaction (described in Example 3) is described. Thus, this method was used to quantitate ketol-isomerase activity in the A. fumigatus cell extract.

A modified Morgan-Elson assay was used to determine GluN-6-P concentration (Daniels et al., *J. Clin. Invest.*, 97:1235–1241 [1996]). Briefly, 5 $\mu$L of saturated NaHCO$_3$ solution and 5 $\mu$L of cold 5% acetic acid were combined with 30 $\mu$l of the ketol-isomerase reaction supernatant, as described in Example 3. The mixture was incubated at room temperature for 3 minutes, then boiled for 3 minutes, followed by the addition of 50 $\mu$L of 0.27 M sodium borate. Following addition of the sodium borate solution, the tubes were boiled again for 8 minutes, then cooled to room temperature. Then, 400 $\mu$L of Ehrlich's reagent (1.0 g p-dimethylaminobenzaldehyde dissolved in 1.25 mL 10 N HCl, then diluted to 100 mL with glacial acetic acid) was added, followed by incubation at 37° C. for 20 minutes and colorimetric analysis (OD$_{585\ nm}$). Color development is directly proportional to the generation of GluN-6-P from the ketol-isomerase assay. Samples of GluN-6-P of known concentration were analyzed in parallel as standardization values to determine absolute GluN-6-P concentration in the experimental samples.

EXAMPLE 5

Direct Comparison of Morgan-Elson and Nitro BT Assays

In this Example, the modified Morgan-Elson and nitro BT assays were used to quantitate the concentrations of glucosamine-6-phosphate (GlcN-6-P) and glutamate, respectively, in a sample. In particular, this comparison was made after the ketol-isomerase reaction described in Example 3 was conducted. The Morgan-Elson and the nitro BT assays were conducted according to the protocols described in Examples 4 and 1, respectively. Thus, ketol-isomerase activity in the *A. fumigatus* cell extract was determined using both methods, and the results of these two assays were compared. This experiment tested the usefulness (i.e., reliability) of the nitro BT assay to quantitate ketol-isomerase activity, using the Morgan-Elson assay as a comparison.

The Morgan-Elson assay was conducted as described in Example 4. The nitro BT assay was performed in the wells of a 96 well microtiter plate, where 50 $\mu$L of the ketol-isomerase reaction mixture was combined with 50 $\mu$L of the nitro BT reaction buffer (pH 8.2), incubated at 37° C. for 90 minutes, followed by the quantitation of color development at OD$_{585\ nm}$.

The results of this side-by-side comparison are shown in FIG. 4. As can be seen in this Figure, there were no discrepancies between the stoichiometric quantities of glutamate and GlcN-6-P following the ketol-isomerase reaction with *A. fumigatus* cell extract, as determined by the nitro BT and the Morgan-Elson assays, respectively. In a control ketol-isomerase reaction, the substrate glutamine was omitted. In that control reaction, neither glutamate nor GlcN-6-P were detected (data not shown). From these results, it is apparent that the nitro BT assay is able to quantitate ketol-isomerase activity at least as effectively as the Morgan-Elson assay.

EXAMPLE 6

Detection of Inhibitors of Ketol-Isomerase by the Nitro BT Assay

In this Example, experiments conducted to determine whether the nitro BT colorimetric assay is able to detect whether a compound has the ability to suppress the ketol-isomerase activity from an *A. fumigatus* cell extract. In this Example, the compound being tested was UDP-N-acetylglucosamine (UDP-GlcNAc), which is known to cause feedback inhibition of *Neurospora crassa* ketol-isomerase (Endo et al., *J. Bacteriol.*, 103:588–594 [1970]). The UDP-GlcNAc was tested at a concentration range from 0 to 10 mM.

In this experiment, 50 $\mu$L aliquots of a ketol-isomerase reaction mixture containing 10 mM Fru-6-P, 10 mM Gln, 0.3 mg/mL crude *A. fumigatus* extract, and various concentrations of UDP-GlcNAc were incubated at 37° C. for 60 minutes. The reaction was terminated by heating at 70° C. for 15 min, followed by addition of 50 $\mu$L of nitro BT reaction buffer, pH 8.2 (See, Example 1). After incubation at 37° C. for 90 minutes, the color development was quantitated by $OD_{585\ nm}$.

The results of this assay are shown in a bar-graph format in FIG. 5. Each data point is the mean of three samples; the standard deviation of each data point is indicated by vertical lines. As indicated in the Figure, the ketol-isomerase activity contained in the A. fumigatus crude extract was inhibited by UDP-GlcNAc in a dose-dependent manner. The $IC_{50}$ (the concentration of compound which inhibits enzymatic activity by 50% relative to an untreated control) was 0.48 mM. This inhibitory effect is similar to that previously reported for UDP-GlcNAc to inhibit ketol-isomerase activity in crude cell extract of Candida albicans ATCC10261 yeast-like cells ($IC_{50}$=0.69 mM; Milewski et al., J. Biol. Chem., 274:4000–4008 [1999]). These results indicate that ketol-isomerase inhibitors can be successfully detected using the nitro BT assay of the present invention.

EXAMPLE 7

Assays for Identifying Compounds Having Antibacterial Activity

In this Example, protocols are provided for the assay of antibacterial activity. These assays can be used to screen compounds previously identified as having ketol-isomerase-inhibiting activity, to determine whether these compounds also contain antibacterial activity. Such antibacterial assays are common in the art, and it is not intended that the present invention be limited to those assays described herein.

Agar diffusion and microbroth dilution antibacterial activity assays are provided. The microbroth dilution method can be used in preliminary examination, as the method is more readily adaptable for large-scale screening. The microbroth dilution method is also suitable for use when a quantitative result is desired, as this method permits the quantitation of antibacterial activity by the determination of a "minimum inhibitory concentration" (i.e., MIC). The incubation periods, media and temperatures recited in these methods are intended to be exemplary only, as other bacterial growth conditions, as known in the art, also find use with the present invention.

Agar Diffusion Method—Muller-Hinton agar medium (Difco) is autoclaved and allowed to cool to 40–50° C. While the medium is still molten, a bacterial suspension (e.g., S. aureus, E. coli or P. aeruginosa) is inoculated into the medium and mixed to give a final concentration of $10^5$–$10^6$ cells/mL. A suitable volume of the still-molten mixture is poured into culture dishes on a level surface to give a uniform agar depth of about 4 mm, and allowed to cool to room temperature. Two μL of a test solution containing the candidate antibacterial compound is placed onto the agar surface. Alternatively, absorbent disks containing known amounts of the candidate test antimicrobials are placed on the agar surface. The plates are incubated at 35–37° C. for 16–24 hours. Antibacterial activity is determined by measuring the diameters (i.e., zones) of growth inhibition.

Microbroth Dilution Method—Serial dilutions of a solution containing a candidate antibacterial compound are made in 100 μL of Muller-Hinton liquid broth (Difco) in the wells of a 96-well microtiter plate. An additional 5 μL of physiological saline containing ca. $10^7$cells/mL of a test bacterial strain (e.g., S. aureus, E. coli or P. aeruginosa) are then added to the wells. Plates are incubated at 35–37° C. for 16–24 hours. The amount of growth in each well is determined either by eye or by using an automated microplate reader capable of measuring turbidity and/or light absorbance.

EXAMPLE 8

Assays for Identifying Compounds Having Antifungal Activity

In this Example, protocols are provided for the assay of antifungal activity. These assays can be used to screen compounds previously identified as having ketol-isomerase-inhibiting activity, to determine whether these compounds also contain antifungal activity. Such antifungal assays are common in the art, and it is not intended that the present invention be limited to the assays described herein.

Agar diffusion and microbroth dilution antifungal activity assays are provided in this Example. The microbroth dilution method can be used in preliminary examination, as the method is more readily adaptable for large-scale screening. The microbroth dilution method is also suitable for use when a quantitative result is desired, as this method permits the quantitation of antifungal activity by the determination of a "minimum inhibitory concentration" (i.e., MIC). The incubation periods, media and temperatures recited in these methods are intended to be exemplary only, as other fungal growth conditions, as known in the art, also find use with the present invention.

Agar Diffusion Method—RPMI medium (Life Technologies) containing 1.5% agar is autoclaved and allowed to cool to 40–50° C. While the medium is still molten, a fungal suspension (e.g., A. fumigatus or C. albicans) is inoculated into the medium and mixed to give a final concentration of $10^6$ cells/mL. From this still-molten mixture, a suitable volume is poured into culture dishes on a level surface to give a uniform agar depth of about 4 mm, and allowed to cool to room temperature. Two μL of a test solution containing the candidate antibacterial compound is placed onto the agar surface. Alternatively, absorbent disks containing known concentrations of the candidate test antimicrobials are placed on the agar surface. The plates are incubated for 18–24 hours at 35° C. (C. albicans) or 37° C. (A. fumigatus). Antifungal activity is determined by measuring the diameters (i.e., zones) of growth inhibition in the agar.

Microbroth Dilution Method—Serial dilutions of a candidate antifungal compound are made in 100 μL of RPMI medium (Life Technologies) in the wells of a 96-well microtiter plate. An additional 100 μL RPMI medium containing $2 \times 10^4$ conidia/ml of a test fungal strain is then added to these wells. Conidia from C. albicans, A. fumigatus or any other suitable fungal species, are suitable for use in this assay. Plates are incubated for 48 hours with gentle shaking at 37° C. The amount of growth in each well is estimated either by eye, by microscope examination, or by using an automated 96-well microplate reader capable of measuring turbidity and/or light absorbance. In some embodiments, the methods are adapted so as to allow high throughput screening of large numbers of compounds. In additional embodiments, robotic automation is also used.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in enzymology, medical microbiology or related fields are intended to be within the scope of the following claims.

What is claimed is:

1. A method for identification of a compound which inhibits microbial ketol-isomerase activity, comprising the sequential steps of:
   a) providing:
      i) a microbial ketol-isomerase,
      ii) fructose-6-phosphate,
      iii) glutamine,
      iv) glutamate dehydrogenase,
      v) nicotinamide adenine dinucleotide,
      vi) nitro blue tetrazolium chloride,
      vii) phenazine methosulfate, and
      viii) a candidate compound;
   b) preparing a first and a second reaction mixture, wherein said first reaction mixture comprises said microbial ketol-isomerase, said fructose-6-phosphate and said glutamine, and wherein said second reaction mixture comprises said microbial ketol-isomerase, said fructose-6-phosphate, said glutamine and said candidate compound;
   c) exposing said first and second reaction mixtures to conditions suitable for production of glucosamine-6-phosphate and glutamate;
   d) inactivating said microbial ketol-isomerase in said first and second reaction mixtures;
   e) combining said first and second reaction mixtures with said glutamate dehydrogenase, said nicotinamide adenine dinucleotide, said nitro blue tetrazolium chloride, and said phenazine methosulfate under conditions suitable for production of a chromogenic product, wherein the quantity of said chromogenic product produced is proportional to activity of said microbial ketol-isomerase;
   f) comparing ketol-isomerase activities in said first and second reaction mixtures, and
   g) identifying a candidate compound which inhibits microbial ketol-isomerase activity, wherein the microbial ketol-isomerase activity of said first reaction mixture is greater than the microbial ketol-isomerase activity of said second reaction mixture.

2. The method of claim 1, wherein said microbial ketol-isomerase comprises a crude microbial cell lysate, selected from the group consisting of fungal cell lysates and bacterial cell lysates.

3. The method of claim 2, wherein said crude microbial cell lysate is selected from the group consisting of Aspergillus cell lysates, Candida cell lysates, Cryptococcus cell lysates, Histoplasma cell lysates, Pneumocystis cell lysates, Rhizopus cell lysates, Saccharomyces cell lysates, Schizosaccharomyces cell lysates, Escherichia cell lysates, Staphylococcus cell lysates and Pseudomonas cell lysates.

4. The method of claim 1, wherein said inactivating step is selected from the group consisting of boiling and heating to 70° C.

5. The method of claim 1, further comprising a clarifying step after the inactivating step, wherein said clarifying step is selected from the group consisting of centrifugation, filtration and a combination thereof.

6. The method of claim 1, further comprising testing said compound which inhibits said microbial ketol-isomerase activity, for antimicrobial activity using a testing means.

7. The method of claim 6, wherein said testing means comprises at least one method selected from the group consisting of agar diffusion assays, broth dilution assays, in vivo mouse candidosis assays, and in vivo mouse aspergillosis assays.

8. The method of claim 1, further comprising the steps of:
   h) providing a second ketol-isomerase selected from the group consisting of plant ketol-isomerases and animal ketol-isomerases;
   i) preparing a third and a fourth reaction mixture, wherein said third reaction mixture comprises said second ketol-isomerase, said fructose-6-phosphate and said glutamine, and wherein said fourth reaction mixture comprises said second ketol-isomerase, said fructose-6-phosphate, said glutamine and said candidate compound,
   j) exposing said third and fourth reaction mixtures to conditions suitable for production of glucosamine-6-phosphate and glutamate,
   k) inactivating said second ketol-isomerase in said third and fourth reaction mixtures,
   l) combining said third and fourth reaction mixtures with said glutamate dehydrogenase, said nicotinamide adenine dinucleotide, said nitro blue tetrazolium chloride, and said phenazine methosulfate under conditions suitable for production of a chromogenic product, wherein the quantity of said chromogenic product is proportional to the activity of said second ketol-isomerase,
   m) comparing ketol-isomerase activities in said third and fourth reaction mixtures, and
   n) identifying a compound which preferentially inhibits said microbial ketol-isomerase activity compared to said second ketol-isomerase activity.

9. The method of claim 8, wherein said animal ketol-isomerases are mammalian ketol-isomerases.

10. The method of claim 9, wherein said mammalian ketol-isomerases are selected from the group consisting of rat ketol-isomerases and human ketol-isomerases.

11. The method of claim 8, wherein said second ketol-isomerase comprises a cell lysate.

12. The method of claim 8, wherein said second ketol-isomerase is purified.

13. The method of claim 8, wherein said second ketol-isomerase is a recombinant ketol-isomerase.

14. The method of claim 13, wherein said recombinant ketol-isomerase is a recombinant human ketol-isomerase.

15. The method of claim 8, wherein said inactivating step is selected from the group consisting of boiling and heating to 70° C.

16. The method of claim 8, further comprising a clarifying step after the inactivating step, wherein said clarifying step is selected from the group consisting of centrifugation, filtration and a combination thereof.

17. The method of claim 8, further comprising testing said compound which preferentially inhibits said microbial ketol isomerase activity, for antimicrobial activity using a testing means.

18. The method of claim 17, wherein said testing means comprises at least one method selected from the group consisting of agar diffusion assays, broth dilution assays, in vivo mouse candidosis assays, and in vivo mouse aspergillosis assays.

19. A method for identification of a compound which inhibits ketol-isomerase activity, comprising the steps of:
  a) providing:
    i) a sample comprising a ketol-isomerase,
    ii) fructose-6-phosphate,
    iii) glutamine,
    iv) glutamate dehydrogenase,
    v) nicotinamide adenine dinucleotide,
    vi) a redox-sensitive chromogenic substrate,
    vii) phenazine methosulfate, and
    viii) a candidate compound;
  b) preparing a first and a second reaction mixture, wherein said first reaction mixture comprises said sample, said fructose-6-phosphate and said glutamine, and wherein said second reaction mixture comprises said sample, said fructose-6-phosphate, said glutamine and said candidate compound;
  c) exposing said first and second reaction mixtures to conditions suitable for production of glucosamine-6-phosphate and glutamate;
  d) inactivating said ketol-isomerase in said first and second reaction mixtures;
  e) combining said first and second reaction mixtures with said glutamate dehydrogenase, said nicotinamide adenine dinucleotide, said tetrazolium salt, and said phenazine methosulfate under conditions suitable for production of a chromogenic product, wherein the quantity of said chromogenic product produced is proportional to activity of said ketol-isomerase;
  f) measuring the amount of said chromogenic product in said first and second reaction mixtures; and
  g) identifying a candidate compound which inhibits ketol isomerase activity, wherein the amount of said chromogenic product in said first reaction mixture is greater than the amount of said chromogenic product in said second reaction mixture.

20. The method of claim 19, wherein said measuring is accomplished by spectrophotometric analysis.

21. The method of claim 19, wherein said sample is selected from the group consisting of a fungal sample, a bacterial sample, an animal sample and a plant sample.

22. The method of claim 19, wherein said ketol-isomerase is in a form selected from the group consisting of a crude cell lysate, a purified ketol-isomerase and a recombinant ketol-isomerase.

23. The method of claim 19, wherein said redox-sensitive chromogenic substrate is nitro blue tetrazolium chloride.

24. The method of claim 19, wherein said redox-sensitive chromogenic substrate is selected from the group consisting of 3-(4,5-dimethyl-2-thiazolyl(-2,5-diphenyl-2H-tetrazolium bromide and sodium 3,3-[(phenylamino)carbonyl]-3,4-tetrazolium-bis(4-methoxy-6-nitro)benzenesulfonic acid hydrate.

* * * * *